US007972830B2

(12) United States Patent
Meier et al.

(10) Patent No.: US 7,972,830 B2
(45) Date of Patent: Jul. 5, 2011

(54) THERMOSTABLE TAQ POLYMERASE FRAGMENT

(75) Inventors: Thomas Meier, Munich (DE); Waltraud Ankenbauer, Penzberg (DE); Annette Deufel, Munich (DE); Dieter Heindl, Paehl (DE); Gisela Betzl, Andechs (DE); Rainer Schmuck, Benediktheuern (DE); Bernd Schneidinger, Wolfratshausen (DE); Jessica Strey, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1145 days.

(21) Appl. No.: 10/917,157

(22) Filed: Aug. 12, 2004

(65) Prior Publication Data

US 2005/0037412 A1 Feb. 17, 2005

(30) Foreign Application Priority Data

Aug. 12, 2003 (EP) .................................... 03017636

(51) Int. Cl.
*C12N 9/12* (2006.01)
(52) U.S. Cl. .................... 435/194; 530/350; 435/183
(58) Field of Classification Search .................. None
See application file for complete search history.

(56) References Cited

U.S. PATENT DOCUMENTS

| | | | |
|---|---|---|---|
| 4,458,066 | A | 7/1984 | Caruthers et al. |
| 4,683,195 | A | 7/1987 | Mullis et al. |
| 4,683,202 | A | 7/1987 | Mullis |
| 4,889,818 | A | 12/1989 | Gelfand et al. |
| 4,965,188 | A | 10/1990 | Mullis et al. |
| 5,079,352 | A | 1/1992 | Gelfand et al. |
| 5,338,671 | A | 8/1994 | Scalice et al. |
| 5,436,149 | A | 7/1995 | Barnes |
| 5,616,494 | A | 4/1997 | Barnes |
| 5,618,676 | A | 4/1997 | Hitzeman et al. |
| 5,677,152 | A | 10/1997 | Birch et al. |
| 5,773,258 | A | 6/1998 | Birch et al. |
| 5,854,018 | A | 12/1998 | Hitzeman et al. |
| 5,856,123 | A | 1/1999 | Hitzeman et al. |
| 5,885,813 | A | 3/1999 | Davis et al. |
| 5,919,651 | A | 7/1999 | Hitzeman et al. |
| 6,183,998 | B1 | 2/2001 | Ivanov et al. |
| 6,479,264 | B1 | 11/2002 | Louwrier |

FOREIGN PATENT DOCUMENTS

| | | |
|---|---|---|
| EP | 0771870 B1 | 5/1987 |
| EP | 0229701 B1 | 7/1987 |
| EP | 0237362 B2 | 9/1987 |
| EP | 0258017 B1 | 3/1988 |
| EP | 0745676 B1 | 12/1996 |
| EP | 0894860 A1 | 2/1999 |
| EP | 1069131 A1 | 7/2000 |
| JP | 2003009880 A1 | 1/2003 |
| JP | 2003199592 A1 | 7/2003 |
| WO | WO 91/02090 | 2/1991 |
| WO | WO 91/05210 | 4/1991 |
| WO | WO 91/05753 | 5/1991 |
| WO | WO 92/06200 | 4/1992 |
| WO | WO 99/64438 | 12/1999 |

OTHER PUBLICATIONS

Qiagen Product Guide, 1997, pp. 106-110.*
Ansorge, W. et al., "Automated DNA sequencing: ultrasensitive detection of fluroscent bands during electrophoresis," Nuc. Acids REs. 15 (1987) 4593-4602.
Barr et al., "7-Deaza-2;-Deoxyguanosine-5'-Triphosphate: Enhanced Resolution in M13 Dideoxy Sequencing," BioTechniques 4 (1986) 428-432.
Beaucage et al., "Deoxynucleoside phosphoramidites—a new class of key intermediates for deoxypolynucleotide synthesis," Tetrahedron Letters 22 (1981) 1859-1862.
Bessman et al., "Enzamatic Synthesis of Deoxyribonucleic Acid," J. Biol. Chem. 223 (1957) 171-177.
Buttin, G. et al., "Enzymatic Synthesis of Deoxyribonucleic Acid," J. Biol. Chem. 241 (1966) 5419-5427.
Chou et al., "Prevention of pre-PCR mis-priming and primer dimerization improves low-copy-number amplifications," Nucleic Acids Res. 20 (1992) 1717-1723.
Cohen, S.N. et al., "Nonchromosomal Antibiotic Resistance in Bacteria: Genetic Transformation of *Escherichia coli* by R-Factor DNA," Proc. Natl. Acad. Sci. USA 69 (1972) 2110-2114.
Dabrowski, S. et al., "Recombinant His-tagged DNA polymerase. I. Cloning, purification and partial characterization of *Thermus thermophilus* recombinant DNA polymerase," Acta Biochimica Polonica 45 (1998) 653-660.
Graham et al., "A New Technique fro the Assay of Infectivity of Human Adenovirus 5 DNA," Virology 52 (1973).
Gyllensten, U.B. et al., "Generation of single-stranded DNA by the polymerase chain reaction and its application to direct sequence of the HLA-DQA Locus," Proc. Natl. Acad. Sci. USA 85 (1988)7652-7656.
Hsiao, C.L. et al., "High-frequency transformation of yeast by plasmids containing the cloned yeast ARG4 gene," Proc. Natl. Acad. Sci. USA76 (1979) 3829-3833.
Innis, M.A. et al., "DNA sequencing with *Thermus aquaticus* DNA polymerase and direct sequencing of polymerase chain reaction-amplified DNA," Proc. Natl. Acad. Sci. USA 85 (1988) 9436-9440.
Kaledin et al., "N-Terminal methionine in recombinant proteins expressed in two different *Escherichia coli* strains," Chemical Abstract 93, No. 401690 (1989).
Kuhn et ., "DNA Helicases," CSH-Quantitative Biology 43 (1978) 63.
Lawyer, F.C. et al., "Isolation, Characterization, and Expression in *Escherichia coli* of the DNA Plymerase Gene from *Thermus aquaticus*," J. Biol. Chem. 264 (1989) 6427-6437.

(Continued)

Primary Examiner — Richard G Hutson

(57) ABSTRACT

It was found that a fragment of native *Thermus aquaticus* DNA polymerase (TaqWT) lacking 288 N-terminal amino acids (TaqΔ288) possesses an increased thermostability over TaqWT, TaqΔ279, and TaqΔ289. The present invention therefore provides TaqΔ288, recombinant expression vectors encoding the same or derivatives thereof, as well as purification protocols for TaqΔ288. The invention also encompasses kits containing TaqΔ288 as well as the use of TaqΔ288 and kits containing TaqΔ288. In addition, the invention encompasses methods for the sequencing a nucleic acid template and methods for amplifying a target nucleic acid.

4 Claims, 1 Drawing Sheet

OTHER PUBLICATIONS

Loh, E., "Anchored PCR: Amplicication with Single-Sided Specificty," Methods: A companion to Methods in Enzymology (1991) 2, pp. 11-19.

Maniatis et al., Molecular Cloning: A Laboratory Manual, Cold Spring Jarbor Laboratory, Clold Spring Harbor, NY, 1982, pp. 280-281.

McConlogue, L. et al., "Structure-independent DNA amplifications by PCR using 7'deaza-2'- deoxyguanosine," Nucleic Acids Res. 16 (1988) 9869.

Mills, D.R., et al., "Structure-independent nucleotide sequence analysis," Proc. Natl. Acad. Sci. USA 76(1979) 2232-2235.

Ochman, H. at al., "Genetic Applications of an Inverse Polymerase Chain Reaction," Genetics 120 (1998) 621-623.

Prober, J.M. et al., "A System for Rapid DNA Sequencing with Fluorescent Chain-Terminating Dideoxynucleotides," Science 238 (1987) 336-342.

Radding, C.M., "Homologous Paring and Strand Exchange in Genetic Recombination," Ann. Rev. Genetics16 (1982) 405-437.

Saiki, R.K. et al., "Enzymatic Amplification of B-Globin Genomic Sequences and Restriction Site Analysis for Diagnosis of Sickle Cell Anemia," Science 230 (1985) 1350-1354.

Sanger, F. et al., "DNA sequencing with chain-terminating inhibitors," Proc. Natl. Acad. Sci. USA 74 (1977) 5463-5467.

Sharkey, D. J. et al., "Antibodies as Thermolabile Switches: High Temperature Triggering for the Polymerase Chain Reaction," BioTechnology 12 (1994) 506-509.

Shaw, C.H. et al., "A general method for the transfer of cloned genes to plant cells," Gene 23 (1983) 315-330.

Smith, L. M. et al., "Fluorescence detection in automated DNA sequence analysis," Nature 321 (1986) 674-679.

Tabor, S. at al., ., "DNA sequence analysis with a modified bacteriophage T7 DNA polymerase" Proc. Natl. Sci. USA 84 (1987) 4767-4771.

van Solingen, P. et al., "Fusion of Yeast Speroplasts," J. Bact. 130 (1997) 946-947.

Vassileva-Anatassova et al., "N-terminal methionine in recombinant proteins expressed in two different *Escherichia coli* strains," Journal of Biotechnology 69 (1999) 63-67.

Yanisch-Perron, C. at al., "Improved M13 phage cloning vectors and host strains: nucleotide sequences of the M13mp18 and pUC19 vectors," Gene 33 (1985) 103-119.

QIAexpress Ni-NTA Technology Reliable 6xHis-tagged Protein Purification, 12pp.

Li,Ying et al., "Crystal structures of the Klenow fragment of *Thermus aquaticus* DNA polymerase I complexed with deoxyribonucleoside triphosphates," Protein Science (1998) 7:1116-1123.

Villbrandt, B. et al., "Investigations of the Thermostability and Function of Truncated *Thermus aquaticus* DNA Polymerase Fragments," Protein Engineering, vol. 10, No. 11, pp. 1281-1288.

* cited by examiner

SEQUENCE LISTING

<160> NUMBER OF SEQ ID NOS: 10

<210> SEQ ID NO 1
<211> LENGTH: 1638
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaaagcccca aggccctgga ggaggccccc tggcccccgc cggaagggc cttcgtgggc       60 tttgtgcttt cccgcaagga gcccatgtgg gccgatcttc tggccctggc cgccgccagg      120
gggggccggg tccaccgggc ccccgagcct tataaagccc tcagggacct gaaggaggcg      180 cggggggcttc tcgccaaaga cctgagcgtt ctggccctga gggaaggcct tggcctcccg      240
cccggcgacg acccccatgct cctcgcctac ctcctggacc cttccaacac cacccccgag      300
ggggtggccc ggcgctacgg cggggagtgg acggaggagg cggggagcg ggccgccctt      360 tccgagaggc tcttcgccaa cctgtggggg aggcttgagg gggaggagag gctcctttgg      420
ctttaccggg aggtggagag gccccttttcc gctgtcctgg cccacatgga ggccacgggg      480
gtgcgcctgg acgtggccta tctcagggcc ttgtcctgg aggtggccga ggagatcgcc      540
cgcctcgagg ccgaggtctt ccgcctggcc ggccacccct tcaacctcaa ctcccgggac      600

```
cagctggaaa gggtcctctt tgacgagcta gggcttcccg ccatcggcaa gacggagaag      660
accggcaagc gctccaccag cgccgccgtc ctggaggccc tccgcgaggc ccaccccatc      720
gtggagaaga tcctgcagta ccgggagctc accaagctga agagcaccta cattgacccc      780
ttgccggacc tcatccaccc caggacgggc cgcctccaca cccgcttcaa ccagacggcc      840
acggccacgg gcaggctaag tagctccgat cccaacctcc agaacatccc cgtccgcacc      900
ccgcttgggc agaggatccg ccgggccttc atcgccgagg aggggtggct attggtggcc      960
ctggactata gccagataga gctcaggggtg ctggcccacc tctccggcga cgagaacctg     1020
atccgggtct tccaggaggg gcgggacatc cacacggaga ccgccagctg gatgttcggc     1080
gtcccccggg aggccgtgga cccctgatg cgccgggcgg ccaagaccat caacttcggg      1140
gtcctctacg gcatgtcggc ccaccgcctc tcccaggagc tagccatccc ttacgaggag     1200
gcccaggcct tcattgagcg ctactttcag agcttcccca aggtgcgggc ctggattgag     1260
aagaccctgg aggagggcag gaggcggggg tacgtggaga ccctcttcgg ccgccgccgc     1320
tacgtgccag acctagaggc ccgggtgaag agcgtgcggg aggcggccga gcgcatggcc     1380
ttcaacatgc ccgtccaggg caccgccgcc gacctcatga gctggctat ggtgaagctc      1440 ttccccaggc tggaggaaat ggggggccagg atgctccttc aggtccacga cgagctggtc     1500
ctcgaggccc caaaagagag ggcggaggcc gtggcccggc tggccaagga ggtcatggag     1560
ggggtgtatc ccctggccgt gccctggag gtggaggtgg ggataggggga ggactggctc     1620 tccgccaagg agtaatga                                                   1638

<210> SEQ ID NO 2
<211> LENGTH: 544
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ser Pro Lys Ala Leu Glu Glu Ala Pro Trp Pro Pro Glu Gly
1               5                   10                  15

Ala Phe Val Gly Phe Val Leu Ser Arg Lys Glu Pro Met Trp Ala Asp
            20                  25                  30

Leu Leu Ala Leu Ala Ala Ala Arg Gly Gly Arg Val His Arg Ala Pro
        35                  40                  45

Glu Pro Tyr Lys Ala Leu Arg Asp Leu Lys Glu Ala Arg Gly Leu Leu
    50                  55                  60

Ala Lys Asp Leu Ser Val Leu Ala Leu Arg Glu Gly Leu Gly Leu Pro
65                  70                  75                  80

Pro Gly Asp Asp Pro Met Leu Leu Ala Tyr Leu Leu Asp Pro Ser Asn
                85                  90                  95

Thr Thr Pro Glu Gly Val Ala Arg Arg Tyr Gly Gly Glu Trp Thr Glu
            100                 105                 110

Glu Ala Gly Glu Arg Ala Ala Leu Ser Glu Arg Leu Phe Ala Asn Leu
        115                 120                 125

Trp Gly Arg Leu Glu Gly Glu Glu Arg Leu Leu Trp Leu Tyr Arg Glu
    130                 135                 140

Val Glu Arg Pro Leu Ser Ala Val Leu Ala His Met Glu Ala Thr Gly
145                 150                 155                 160

Val Arg Leu Asp Val Ala Tyr Leu Arg Ala Leu Ser Leu Glu Val Ala
                165                 170                 175
```

Glu Glu Ile Ala Arg Leu Glu Ala Glu Val Phe Arg Leu Ala Gly His
            180                 185                 190

Pro Phe Asn Leu Asn Ser Arg Asp Gln Leu Glu Arg Val Leu Phe Asp
            195                 200                 205

Glu Leu Gly Leu Pro Ala Ile Gly Lys Thr Glu Lys Thr Gly Lys Arg
        210                 215                 220

Ser Thr Ser Ala Ala Val Leu Glu Ala Leu Arg Glu Ala His Pro Ile
225                 230                 235                 240

Val Glu Lys Ile Leu Gln Tyr Arg Glu Leu Thr Lys Leu Lys Ser Thr
                245                 250                 255

Tyr Ile Asp Pro Leu Pro Asp Leu Ile His Pro Arg Thr Gly Arg Leu
            260                 265                 270

His Thr Arg Phe Asn Gln Thr Ala Thr Ala Thr Gly Arg Leu Ser Ser
            275                 280                 285

Ser Asp Pro Asn Leu Gln Asn Ile Pro Val Arg Thr Pro Leu Gly Gln
        290                 295                 300

Arg Ile Arg Arg Ala Phe Ile Ala Glu Glu Gly Trp Leu Leu Val Ala
305                 310                 315                 320

Leu Asp Tyr Ser Gln Ile Glu Leu Arg Val Leu Ala His Leu Ser Gly
                325                 330                 335

Asp Glu Asn Leu Ile Arg Val Phe Gln Glu Gly Arg Asp Ile His Thr
            340                 345                 350

Glu Thr Ala Ser Trp Met Phe Gly Val Pro Arg Glu Ala Val Asp Pro
        355                 360                 365

Leu Met Arg Arg Ala Ala Lys Thr Ile Asn Phe Gly Val Leu Tyr Gly
        370                 375                 380

Met Ser Ala His Arg Leu Ser Gln Glu Leu Ala Ile Pro Tyr Glu Glu
385                 390                 395                 400

Ala Gln Ala Phe Ile Glu Arg Tyr Phe Gln Ser Phe Pro Lys Val Arg
                405                 410                 415

Ala Trp Ile Glu Lys Thr Leu Glu Glu Gly Arg Arg Arg Gly Tyr Val
            420                 425                 430

Glu Thr Leu Phe Gly Arg Arg Arg Tyr Val Pro Asp Leu Glu Ala Arg
        435                 440                 445

Val Lys Ser Val Arg Glu Ala Ala Glu Arg Met Ala Phe Asn Met Pro
450                 455                 460

Val Gln Gly Thr Ala Ala Asp Leu Met Lys Leu Ala Met Val Lys Leu
465                 470                 475                 480

Phe Pro Arg Leu Glu Glu Met Gly Ala Arg Met Leu Leu Gln Val His
            485                 490                 495

Asp Glu Leu Val Leu Glu Ala Pro Lys Glu Arg Ala Glu Ala Val Ala
        500                 505                 510

Arg Leu Ala Lys Glu Val Met Glu Gly Val Tyr Pro Leu Ala Val Pro
        515                 520                 525

Leu Glu Val Glu Val Gly Ile Gly Glu Asp Trp Leu Ser Ala Lys Glu
530                 535                 540

<210> SEQ ID NO 3
<211> LENGTH: 1641
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atggaaagcc caaggccct ggaggaggcc ccctggcccc cgccggaagg ggccttcgtg    60
ggctttgtgc tttcccgcaa ggagcccatg tgggccgatc ttctggccct ggccgccgcc   120 aggggggggcc gggtccaccg gccccccgag ccttataaag ccctcaggga cctgaaggag   180 gcgcggggc ttctcgccaa agacctgagc gttctggccc tgagggaagg ccttggcctc   240
ccgcccggcg acgacccat gctcctcgcc tacctcctgg acccttccaa caccaccccc   300 gaggggggtgg cccggcgcta cggcggggag tggacggagg aggcggggga gcgggccgcc   360
ctttccgaga ggctcttcgc caacctgtgg gggaggcttg aggggagga gaggctcctt   420 tggctttacc gggaggtgga gaggccccctt tccgctgtcc tggcccacat ggaggccacg   480
ggggtgcgcc tggacgtggc ctatctcagg gccttgtccc tggaggtggc cgaggagatc   540
gcccgcctcg aggccgaggt cttccgcctg ccggccacc ccttcaacct caactcccgg   600
gaccagctgg aaagggtcct ctttgacgag ctagggcttc cgccatcgg caagacggag   660 aagaccggca agcgctccac cagcgccgcc gtcctggagg ccctccgcga ggcccacccc   720
atcgtggaga agatcctgca gtaccgggag ctcaccaagc tgaagagcac ctacattgac   780
cccttgccgg acctcatcca ccccaggacg ggccgcctcc acacccgctt caaccagacg   840
gccacggcca cgggcaggct aagtagctcc gatcccaacc tccagaacat ccccgtccgc   900
accccgcttg gcagaggat ccgcggggcc ttcatcgccg aggaggggtg gctattggtg   960
gccctggact atagccagat agagctcagg gtgctggccc acctctccgg cgacgagaac  1020
ctgatccggg tcttccagga ggggcgggac atccacacgg agaccgccag ctggatgttc  1080
ggcgtccccc gggaggccgt ggaccccctg atgcgccggg cggccaagac catcaacttc  1140
ggggtcctct acggcatgtc ggcccaccgc ctctcccagg agctagccat cccttacgag  1200
gaggcccagg ccttcattga gcgctacttt cagagcttcc ccaaggtgcg ggcctggatt  1260
gagaagaccc tggaggaggg caggaggcgg gggtacgtgg agaccctctt cggccgccgc  1320
cgctacgtgc cagacctaga ggcccgggtg aagagcgtgc gggaggcggc cgagcgcatg  1380
gccttcaaca tgcccgtcca gggcaccgcc gccgacctca tgaagctggc tatggtgaag  1440
ctcttcccca ggctggagga aatgggggcc aggatgctcc ttcaggtcca cgacgagctg  1500
gtcctcgagg ccccaaaaga gagggcggag gccgtggccc ggctggccaa ggaggtcatg  1560
gagggggtgt atcccctggc cgtgcccctg gaggtggagg tggggatagg ggaggactgg  1620
ctctccgcca aggagtaatg a                                            1641
```

<210> SEQ ID NO 4
<211> LENGTH: 545
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Glu Ser Pro Lys Ala Leu Glu Glu Ala Pro Trp Pro Pro Pro Glu
1               5                   10                  15

Gly Ala Phe Val Gly Phe Val Leu Ser Arg Lys Glu Pro Met Trp Ala
            20                  25                  30

Asp Leu Leu Ala Leu Ala Ala Ala Arg Gly Gly Arg Val His Arg Ala
        35                  40                  45

Pro Glu Pro Tyr Lys Ala Leu Arg Asp Leu Lys Glu Ala Arg Gly Leu
    50                  55                  60

-continued

```
Leu Ala Lys Asp Leu Ser Val Leu Ala Leu Arg Glu Gly Leu Gly Leu
 65                  70                  75                  80

Pro Pro Gly Asp Asp Pro Met Leu Leu Ala Tyr Leu Leu Asp Pro Ser
                 85                  90                  95

Asn Thr Thr Pro Glu Gly Val Ala Arg Arg Tyr Gly Gly Glu Trp Thr
            100                 105                 110

Glu Glu Ala Gly Glu Arg Ala Ala Leu Ser Glu Arg Leu Phe Ala Asn
        115                 120                 125

Leu Trp Gly Arg Leu Glu Gly Glu Arg Leu Leu Trp Leu Tyr Arg
130                 135                 140

Glu Val Glu Arg Pro Leu Ser Ala Val Leu Ala His Met Glu Ala Thr
145                 150                 155                 160

Gly Val Arg Leu Asp Val Ala Tyr Leu Arg Ala Leu Ser Leu Glu Val
                165                 170                 175

Ala Glu Glu Ile Ala Arg Leu Glu Ala Glu Val Phe Arg Leu Ala Gly
            180                 185                 190

His Pro Phe Asn Leu Asn Ser Arg Asp Gln Leu Glu Arg Val Leu Phe
        195                 200                 205

Asp Glu Leu Gly Leu Pro Ala Ile Gly Lys Thr Glu Lys Thr Gly Lys
210                 215                 220

Arg Ser Thr Ser Ala Ala Val Leu Glu Ala Leu Arg Glu Ala His Pro
225                 230                 235                 240

Ile Val Glu Lys Ile Leu Gln Tyr Arg Glu Leu Thr Lys Leu Lys Ser
                245                 250                 255

Thr Tyr Ile Asp Pro Leu Pro Asp Leu Ile His Pro Arg Thr Gly Arg
            260                 265                 270

Leu His Thr Arg Phe Asn Gln Thr Ala Thr Ala Thr Gly Arg Leu Ser
        275                 280                 285

Ser Ser Asp Pro Asn Leu Gln Asn Ile Pro Val Arg Thr Pro Leu Gly
290                 295                 300

Gln Arg Ile Arg Arg Ala Phe Ile Ala Glu Glu Gly Trp Leu Leu Val
305                 310                 315                 320

Ala Leu Asp Tyr Ser Gln Ile Glu Leu Arg Val Leu Ala His Leu Ser
                325                 330                 335

Gly Asp Glu Asn Leu Ile Arg Val Phe Gln Glu Gly Arg Asp Ile His
            340                 345                 350

Thr Glu Thr Ala Ser Trp Met Phe Gly Val Pro Arg Glu Ala Val Asp
        355                 360                 365

Pro Leu Met Arg Arg Ala Ala Lys Thr Ile Asn Phe Gly Val Leu Tyr
370                 375                 380

Gly Met Ser Ala His Arg Leu Ser Gln Glu Leu Ala Ile Pro Tyr Glu
385                 390                 395                 400

Glu Ala Gln Ala Phe Ile Glu Arg Tyr Phe Gln Ser Phe Pro Lys Val
                405                 410                 415

Arg Ala Trp Ile Glu Lys Thr Leu Glu Glu Gly Arg Arg Arg Gly Tyr
            420                 425                 430

Val Glu Thr Leu Phe Gly Arg Arg Arg Tyr Val Pro Asp Leu Glu Ala
        435                 440                 445

Arg Val Lys Ser Val Arg Glu Ala Ala Glu Arg Met Ala Phe Asn Met
450                 455                 460

Pro Val Gln Gly Thr Ala Ala Asp Leu Met Lys Leu Ala Met Val Lys
465                 470                 475                 480

Leu Phe Pro Arg Leu Glu Glu Met Gly Ala Arg Met Leu Leu Gln Val
                485                 490                 495
```

His Asp Glu Leu Val Leu Glu Ala Pro Lys Glu Arg Ala Glu Ala Val
            500                 505                 510

Ala Arg Leu Ala Lys Glu Val Met Glu Gly Val Tyr Pro Leu Ala Val
            515                 520                 525

Pro Leu Glu Val Glu Val Gly Ile Gly Glu Asp Trp Leu Ser Ala Lys
            530                 535                 540

Glu
545

<210> SEQ ID NO 5
<211> LENGTH: 558
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Arg Gly Ser His His His His His His Ile Glu Gly Arg Glu Ser
1               5                   10                  15

Pro Lys Ala Leu Glu Glu Ala Pro Trp Pro Pro Glu Gly Ala Phe
            20                  25                  30

Val Gly Phe Val Leu Ser Arg Lys Glu Pro Met Trp Ala Asp Leu Leu
            35                  40                  45

Ala Leu Ala Ala Ala Arg Gly Gly Arg Val His Arg Ala Pro Glu Pro
            50                  55                  60

Tyr Lys Ala Leu Arg Asp Leu Lys Glu Ala Arg Gly Leu Leu Ala Lys
65                  70                  75                  80

Asp Leu Ser Val Leu Ala Leu Arg Glu Gly Leu Gly Leu Pro Pro Gly
            85                  90                  95

Asp Asp Pro Met Leu Leu Ala Tyr Leu Leu Asp Pro Ser Asn Thr Thr
            100                 105                 110

Pro Glu Gly Val Ala Arg Arg Tyr Gly Gly Glu Trp Thr Glu Glu Ala
            115                 120                 125

Gly Glu Arg Ala Ala Leu Ser Glu Arg Leu Phe Ala Asn Leu Trp Gly
            130                 135                 140

Arg Leu Glu Gly Glu Glu Arg Leu Leu Trp Leu Tyr Arg Glu Val Glu
145                 150                 155                 160

Arg Pro Leu Ser Ala Val Leu Ala His Met Glu Ala Thr Gly Val Arg
            165                 170                 175

Leu Asp Val Ala Tyr Leu Arg Ala Leu Ser Leu Glu Val Ala Glu Glu
            180                 185                 190

Ile Ala Arg Leu Glu Ala Glu Val Phe Arg Leu Ala Gly His Pro Phe
            195                 200                 205

Asn Leu Asn Ser Arg Asp Gln Leu Glu Arg Val Leu Phe Asp Glu Leu
            210                 215                 220

Gly Leu Pro Ala Ile Gly Lys Thr Glu Lys Thr Gly Lys Arg Ser Thr
225                 230                 235                 240

Ser Ala Ala Val Leu Glu Ala Leu Arg Glu Ala His Pro Ile Val Glu
            245                 250                 255

Lys Ile Leu Gln Tyr Arg Glu Leu Thr Lys Leu Lys Ser Thr Tyr Ile
            260                 265                 270

Asp Pro Leu Pro Asp Leu Ile His Pro Arg Thr Gly Arg Leu His Thr
            275                 280                 285

Arg Phe Asn Gln Thr Ala Thr Ala Thr Gly Arg Leu Ser Ser Ser Asp
            290                 295                 300

```
Pro Asn Leu Gln Asn Ile Pro Val Arg Thr Pro Leu Gly Gln Arg Ile
305                 310                 315                 320

Arg Arg Ala Phe Ile Ala Glu Glu Gly Trp Leu Leu Val Ala Leu Asp
            325                 330                 335

Tyr Ser Gln Ile Glu Leu Arg Val Leu Ala His Leu Ser Gly Asp Glu
            340                 345                 350

Asn Leu Ile Arg Val Phe Gln Glu Gly Arg Asp Ile His Thr Glu Thr
            355                 360                 365

Ala Ser Trp Met Phe Gly Val Pro Arg Glu Ala Val Asp Pro Leu Met
370                 375                 380

Arg Arg Ala Ala Lys Thr Ile Asn Phe Gly Val Leu Tyr Gly Met Ser
385                 390                 395                 400

Ala His Arg Leu Ser Gln Glu Leu Ala Ile Pro Tyr Glu Glu Ala Gln
            405                 410                 415

Ala Phe Ile Glu Arg Tyr Phe Gln Ser Phe Pro Lys Val Arg Ala Trp
            420                 425                 430

Ile Glu Lys Thr Leu Glu Glu Gly Arg Arg Arg Gly Tyr Val Glu Thr
            435                 440                 445

Leu Phe Gly Arg Arg Arg Tyr Val Pro Asp Leu Glu Ala Arg Val Lys
450                 455                 460

Ser Val Arg Glu Ala Ala Glu Arg Met Ala Phe Asn Met Pro Val Gln
465                 470                 475                 480

Gly Thr Ala Ala Asp Leu Met Lys Leu Ala Met Val Lys Leu Phe Pro
            485                 490                 495

Arg Leu Glu Glu Met Gly Ala Arg Met Leu Leu Gln Val His Asp Glu
            500                 505                 510

Leu Val Leu Glu Ala Pro Lys Glu Arg Ala Glu Ala Val Ala Arg Leu
            515                 520                 525

Ala Lys Glu Val Met Glu Gly Val Tyr Pro Leu Ala Val Pro Leu Glu
530                 535                 540

Val Glu Val Gly Ile Gly Glu Asp Trp Leu Ser Ala Lys Glu
545                 550                 555

<210> SEQ ID NO 6
<211> LENGTH: 2499
<212> TYPE: DNA
<213> ORGANISM: Thermus aquaticus

<400> SEQUENCE: 6 atgagggggga tgctgccccct ctttgagccc aagggccggg tcctcctggt ggacggccac      60
cacctggcct accgcacctt ccacgccctg aagggcctca ccaccagccg ggggagccg       120 gtgcaggcgg tctacggctt cgccaagagc ctcctcaagg ccctcaagga ggacggggac      180
gcggtgatcg tggtctttga cgccaaggcc cctccttcc gccacgaggc ctacgggggg       240
tacaaggcgg ccgggcccc cacgccggag gactttcccc ggcaactcgc cctcatcaag      300
gagctggtgg acctcctggg gctggcgcgc tcgaggtcc gggctacga ggcggacgac       360 gtcctggcca gcctggccaa gaaggcggaa aaggagggct acgaggtccg catcctcacc      420
gccgacaaag accttttacca gctcctttcc gaccgcatcc acgtcctcca ccccgagggg      480
tacctcatca cccccggcctg ctttgggaa agtacggcc tgaggcccga ccagtgggcc       540
gactaccggg ccctgaccgg ggacgagtcc gacaaccttc cgggggtcaa gggcatcggg      600
gagaagacgc gaggaagct tctggaggag tgggggagcc tggaagccct cctcaagaac      660
ctggaccggc tgaagcccgc catccgggag aagatcctgg cccacatgga cgatctgaag      720
```

-continued

```
ctctcctggg acctggccaa ggtgcgcacc gacctgcccc tggaggtgga cttcgccaaa      780
aggcgggagc ccgaccggga gaggcttagg gcctttctgg agaggcttga gtttggcagc      840
ctcctccacg agttcggcct tctggaaagc cccaaggccc tggaggaggc ccctggcccc      900
ccgccggaag gggccttcgt gggctttgtg ctttcccgca aggagcccat gtgggccgat      960
cttctggccc tggccgccgc caggggggc cgggtccacc gggcccccga gccttataaa      1020
gccctcaggg acctgaagga ggcgcggggg cttctcgcca agacctgag cgttctggcc       1080 ctgagggaag gccttggcct cccgcccggc gacgacccca tgctcctcgc ctacctcctg      1140
gaccccttcc acaccacccc cgagggggtg gcccggcgct acggcgggga gtggacggag      1200
gaggcggggg agcgggccgc cctttccgag aggctcttcg ccaacctgtg ggggaggctt      1260 gaggggggagg agaggctcct ttggctttac cgggaggtgg agaggcccct ttccgctgtc     1320
ctggcccaca tggaggccac ggggggtgcgc ctggacgtgg cctatctcag ggccttgtcc    1380
ctggaggtgg ccgaggagat cgcccgcctc gaggccgagg tcttccgcct ggccggccac     1440
cccttcaacc tcaactcccg ggaccagctg gaaagggtcc tctttgacga gctagggctt     1500
cccgccatcg gcaagacgga gaagaccggc aagcgctcca ccagcgccgc cgtcctggag    1560
gccctccgcg aggcccaccc catcgtggag aagatcctgc agtaccggga gctcaccaag     1620
ctgaagagca cctacattga ccccttgccg gacctcatcc accccaggac gggccgcctc     1680
cacacccgct tcaaccagac ggccacggcc acgggcaggc taagtagctc cgatcccaac     1740
ctccagaaca tccccgtccg cacccccgctt gggcagagga tccgccgggc cttcatcgcc    1800
gaggaggggt ggctattggt ggccctggac tatagccaga tagagctcag ggtgctggcc     1860
cacctctccg gcgacgagaa cctgatccgg gtcttccagg aggggcggga catccacacg     1920
gagaccgcca gctggatgtt cggcgtcccc cgggaggccg tggaccccct gatgcgccgg     1980
gcggccaaga ccatcaactt cggggtcctc tacggcatgt cggcccaccg cctctcccag     2040
gagctagcca tcccttacga ggaggcccag gccttcattg agcgctactt tcagagcttc     2100
cccaaggtgc gggcctggat tgagaagacc ctggaggagg caggaggcg ggggtacgtg     2160 gagaccctct tcggccgccg ccgctacgtg ccagacctag aggcccgggt gaagagcgtg     2220
cgggaggcgg ccgagcgcat ggccttcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gcccccaaaag agagggcgga ggccgtggcc  2400
cggctggcca aggaggtcat ggagggggtg tatcccctgg ccgtgccct ggaggtggag     2460 gtggggatag ggaggactg gctctccgcc aaggagtga                             2499
```

<210> SEQ ID NO 7
<211> LENGTH: 832
<212> TYPE: PRT
<213> ORGANISM: Thermus aquaticus

<400> SEQUENCE: 7

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60
```

```
Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Gly Leu Ala Arg Leu Glu
            100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
    275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
    355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
    435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
```

485                 490                 495
Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

```
<210> SEQ ID NO 8
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tcgattcggt acgtccgcgc gatcggcgca tatagcgccg atcgcggacg tac         53

<210> SEQ ID NO 9
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Arg Gly Ser His His His His His His Ile Glu Gly Arg
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Ser Pro Lys Ala Leu Glu Glu Ala Pro Trp Pro Pro Pro Glu
1               5                   10                  15
```

THERMOSTABLE TAQ POLYMERASE FRAGMENT

The present invention is directed to the field of molecular biology. Particularly, the invention is directed to a polypeptide with DNA polymerase activity. The invention provides a polypeptide with thermostable DNA polymerase activity whereby thermostability is enhanced. The invention also provides a method to produce said polypeptide.

DNA polymerases from mesophilic microorganisms such as *E. coli* are well known to the art. See, for example, Bessman et al., J. Biol. Chem. 223 (1957) 171-177 and Buttin, G., and Kornberg, A., J. Biol. Chem. 241 (1966) 5419-5427. Also known to the art are DNA polymerases from thermophiles such as the *Thermus aquaticus* species. The use of thermostable enzymes to amplify existing nucleic acid sequences in amounts that are large compared to the amount initially present was described in U.S. Pat. Nos. 4,683,195, 4,683,202, and 4,965,188 which describe the process of the polymerase chain reaction (PCR). Commercial vendors, such as Roche Diagnostics GmbH (Mannheim, Germany) market PCR reagents and publish PCR protocols. Primers, template, nucleoside triphosphates, the appropriate buffer and reaction conditions, and polymerase are used in the PCR process, which involves denaturation of target DNA, hybridization of primers, and synthesis of complementary strands by the polymerase. The extension product of each primer becomes a template for the production of the desired nucleic acid sequence. The patents disclose that, if the polymerase employed is a thermostable enzyme, then polymerase need not be added after every denaturation step, because heat will not destroy the polymerase activity. However, repeated heating as it is the case in the cyclic PCR process will impact on the enzymatic activity of a polymerase, depending on its thermostability. After a given number of PCR cycles, a polymerase with a higher thermostability will retain more enzymatic activity than a polymerase with a lower thermostability. Therefore, thermostability is a desired feature for a polymerase.

U.S. Pat. Nos. 4,889,818 and 5,079,352 describe the isolation and recombinant expression of a thermostable DNA polymerase with a molecular weight of about 94 kDa from *Thermus aquaticus* (Taq DNA polymerase, also referred to as TaqWT) and the use of that polymerase in PCR.

U.S. Pat. Nos. 4,889,818 and 5,079,352 describe the isolation and recombinant expression of a thermostable DNA polymerase with a molecular weight of about 94 kDa from *Thermus aquaticus* (Taq DNA polymerase, also referred to as TaqWT) and the use of that polymerase in PCR.

Particularly, thermostability of Taq DNA polymerase is surpassed by that of other polymerases. While the half life of purified TaqWT at 95° C. is about 40 min in a stabilized preparation and about 20 min in a typical reaction mixture used for LightCycler PCR, other DNA polymerases such as Pwo DNA polymerase (from *Pyrococcus woesei*; Roche Catalogue No. 1664947) is increased. Pwo DNA polymerase exhibits increased thermal stability with a half life of greater than 2 h at 100° C. compared to Taq DNA polymerase with a half life of less than 5 min at this temperature.

WO 91/02090 describes a thermostable DNA polymerase purified from *Thermus aquaticus*. This polymerase is a 80 or 85 kDa degradation product of the intact polymerase (molecular weight of 94 kDa) and is said to have substantially no 5'-3' exonuclease activity. No sequence data is provided on this polymerase.

Lawyer, F. C., et al. have described in J. Biol. Chem. 264 (1989) 6427-6437 the isolation, characterization and expression of the DNA polymerase gene from *Thermus aquaticus* in *E. coli*. The cloning of expression vectors comprising a DNA sequence encoding a Taq DNA polymerase fragment lacking the N-terminus of the native enzyme is also disclosed.

Kaledin et al. have reported in Chemical Abstract 93, No. 40169p (1989) on the purification of a thermostable DNA polymerase enzyme from *Thermus aquaticus* having a molecular weight of about 60-62 kDa. No sequence data is provided for this polymerase.

Chien et al. have reported in Chemical Abstract 85, No. 155559t (1976) on the purification of a thermostable DNA polymerase enzyme from *Thermus aquaticus*. The molecular weight of this enzyme is reported to be 68 kDa as determined by sucrose gradient centrifugation and 63 kDa as determined by gel filtration. No sequence data is provided for this polymerase.

U.S. Pat. No. 5,616,494 teaches an enzymatically active truncated fragment of Taq DNA polymerase which excludes the N-terminal 235 amino acid residues. The purified enzyme is described to be fully active, however having a reduced processivity and lacking 5'-exonuclease activity. When compared with native Taq DNA polymerase, more units of DNA polymerase are necessary for the deletion fragment to complete a PCR amplification reaction. The truncated form with an additional N-terminal methionine was expressed in *E. coli*.

U.S. Pat. No. 5,885,813 discloses enzymatically active truncated forms of Taq DNA polymerase with an N-terminal deletion of 271 and 272 amino acids, both having a tyrosine residue at the position corresponding to native Taq DNA polymerase residue 667 in its dNMP binding site. Both truncated forms were expressed in *E. coli* with an additional methionine-encoding start codon fused to each reading frame.

U.S. Pat. No. 5,079,352 teaches a truncated form of Taq DNA polymerase (Example IX) with a molecular weight of approximately 61 kDa. During purification, this form (also known as the Stoffel fragment) was originally recognized as a proteolytic artifact. N-terminal sequencing revealed that the truncated form arose as a result of proteolytic cleavage between Glu289 and Ser290. The deletion of 289 amino acids from the N-terminus of native Taq DNA polymerase resulted in a fully active DNA polymerase. The document further describes the construction of a vector comprising a DNA encoding the truncated form that is the Stoffel fragment, and an additional methionine-encoding start codon. Using the vector, the truncated form of native Taq DNA polymerase with a molecular weight of approximately 61 kDa was expressed in *E. coli*. In the present text, the Stoffel fragment (commercially available from Applied Biosystems under the name AmpliTaq DNA polymerase) of native Taq DNA polymerase as documented by U.S. Pat. No. 5,079,352 is further referred to as TaqΔ289.

U.S. Pat. No. 5,436,149 teaches an enzymatically active truncated *Thermus aquaticus* DNA polymerase which, however, excludes the N-terminal 279 amino acid residues. The fragment was expressed in *E. coli* with two additional codons encoding a methionine (start codon) and a glycine residue, fused to the reading frame encoding the amino acid corresponding to native Taq DNA polymerase residue 280. In the present text, fragment of native Taq DNA polymerase as documented by U.S. Pat. No. 5,436,149 (also known as Klentaq1 commercially available from AB Peptides, Inc and also as AdvanTaq DNA polymerase commercially available from Clontech, Inc) is further referred to as TaqΔ279. The enzymatic activity of the truncated form is shown to survive repeated exposure to temperatures of 99° C.

In view of the state of the art, there is a desire for a purified, thermostable DNA polymerase that may be used to improve the PCR process described above and to improve the results obtained when using a thermostable DNA polymerase in other recombinant techniques such as DNA sequencing, and other processes of template-dependent elongation of DNA primers by DNA polymerase activity.

The inventors have surprisingly found that a fragment of native Thermus aquaticus DNA polymerase (TaqWT) lacking 288 N-terminal amino acids (TaqΔ288) possesses an increased thermostability over TaqWT, TaqΔ279, and TaqΔ289. The present invention therefore helps to meet the need described above by providing TaqΔ288, recombinant expression vectors encoding the same or derivatives thereof, as well as purification protocols for TaqΔ288. The invention also encompasses kits containing TaqΔ288 as well as the use of TaqΔ288 and kits containing TaqΔ288. In addition, the invention encompasses methods for the sequencing of a nucleic acid template and methods for amplifying a target nucleic acid.

To facilitate understanding of the invention, a number of terms are defined below.

Amino acid identification uses the three-letter abbreviations as well as the single-letter alphabet of amino acids, i.e., Asp D Aspartic acid, Ile I Isoleucine, Thr T Threonine, Leu L Leucine, Ser S Serine, Tyr Y Tyrosine, Glu E Glutamic acid, Phe F Phenylalanine, Pro P Proline, His H Histidine, Gly G Glycine, Lys K Lysine, Ala A Alanine, Arg R Arginine, Cys C Cysteine, Trp W Tryptophan, Val V Valine, Gln Q Glutamine, Met M Methionine, Asn N Asparagine. An amino acid at a particular position in an amino acid sequence is given by its three-letter abbreviation and a number. As an example, referring to the amino acid sequence of native Taq DNA polymerase of SEQ ID NO: 2, "Glu7" denotes the Glutamic acid residue at amino acid position 7.

The terms "cell", "cell line", and "cell culture" can be used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "control sequences" refers to DNA sequences necessary for the expression of an operably linked coding sequence in a particular host cell. The control sequences that are suitable for prokaryotes, for example, include a promoter, optionally an operator sequence, a ribosome binding site, and possibly other sequences. Eukaryotic cells are known to utilize promoters, polyadenylation signals, and enhancers.

The term "expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may also be integrated into the host chromosome.

The term "gene" refers to a DNA sequence that comprises control and coding sequences necessary for the production of a recoverable bioactive polypeptide or precursor. The polypeptide can be encoded by a full length coding sequence or by any portion of the coding sequence so long as the enzymatic activity is retained.

The terms "to place in operable linkage" and "operably linked" refer to the positioning of the coding sequence such that control sequences will function to drive expression of the protein encoded by the coding sequence. Thus, a coding sequence "operably linked" to control sequences refers to a configuration wherein the coding sequences can be expressed under the direction of a control sequence.

The term "non-ionic polymeric detergents" refers to surface-active agents that have no ionic charge and that are characterized for purposes of this invention, by an ability to stabilize TaqΔ288 at a pH range of from about 3.5 to about 9.5, preferably from 4 to 8.5.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be derived synthetically or by cloning.

The term "primer" as used herein refers to an oligonucleotide which is capable of acting as a point of initiation of synthesis when placed under conditions in which primer extension is initiated. An oligonucleotide "primer" may occur naturally, as in a purified restriction digest or be produced synthetically. Synthesis of a primer extension product which is complementary to a nucleic acid strand is initiated in the presence of four different nucleoside triphosphates and a thermostable polymerase enzyme in an appropriate buffer at a suitable temperature. A "buffer" includes cofactors (such as divalent metal ions) and salt (to provide the appropriate ionic strength), adjusted to the desired pH.

A primer is single-stranded for maximum efficiency in amplification, but may alternatively be double-stranded. If double-stranded, the primer is first treated to separate its strands before being used to prepare extension products. The primer is usually an oligodeoxyribonucleotide. The primer must be sufficiently long to prime the synthesis of extension products in the presence of the polymerase enzyme. The exact length of a primer will depend on many factors, such as source of primer and result desired, and the reaction temperature must be adjusted depending on primer length and nucleotide sequence to ensure proper annealing of primer to template. Depending on the complexity of the target sequence, an oligonucleotide primer typically contains 15 to 35 nucleotides. Short primer molecules generally require lower temperatures to form sufficiently stable complexes with template.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The terms "restriction endonucleases" and "restriction enzymes" refer to bacterial enzymes which cut double-stranded DNA at or near a specific nucleotide sequence.

The term "thermostable" polypeptide with DNA polymerase activity refers to an enzyme which is stable to heat and is heat resistant and catalyzes (facilitates) combination of the nucleotides in the proper manner to form primer extension products that are complementary to a template nucleic acid strand. Generally, synthesis of a primer extension product begins at the 3' end of the primer and proceeds in the 5' direction along the template strand, until synthesis terminates. An example for a thermostable DNA polymerase is Taq DNA polymerase (TaqWT) or deletion fragments thereof such as TaqΔ279, TaqΔ289, and the present enzyme, i.e. TaqΔ288.

The assay for DNA polymerase activity uses a DNA oligonucleotide of which the terminal sequences are G+C rich and capable of hybridizing with each other. The oligonucleotide forms a loop when the terminal sequences hybridize. Hybridization leads to a short stretch of double-stranded DNA which ends with a 5' single-stranded overhang. At the same time, on the opposite strand, a terminal 3'-OH function is provided, thus presenting a substrate for DNA polymerases. In the presence of dNTPs and divalent ions in a reaction mixture and under conditions supporting DNA polymerase activity, a DNA polymerase catalyzes the elongation of the strand with the terminal 3'-OH function with nucleotides complementary to the template strand, that is, the strand with the 5' overhang. The reaction proceeds until the 5' overhang anymore in converted into a blunt end.

The assay is based on the principle of fluorescence resonance energy transfer (FRET), triggered by DNA polymerase activity. Generally, as a first and a second label fluorophores are preferred which are capable of interacting to generate FRET. For the assay setting a special oligonucleotide as described above is used in which within the double-stranded portion at a position close to the nucleotides initially providing the 5' single-stranded overhang, a nucleotide or nucleotide analogue is located which is bound to a first fluorophore. Preferably, the first fluorophore is fluorescein. Within the 5' single-stranded overhang and at a position about 10 nucleotides from the fluorophore-labeled first position there is an adenine. Instead of dTTP, the reaction mixture contains labeled dUTP or a mixture of labeled and unlabeled dUTP; dUTP is capable of being incorporated into the opposite strand to pair with said adenine. Preferably, the label bound to dUTP is LightCycler—Red 640 as second fluorophore. Once labeled dUTP is incorporated by DNA polymerase enzymatic activity, the first and the second label are brought into a proximity which supports FRET. Oligonucleotide molecules with incorporated labeled dUTP can be measured by quantifying FRET using light of a defined excitation wavelength specific for fluorescein but not LightCycler—Red 640 and measuring emitted light at the emission wavelength of Light-Cycler—Red 640 using a fluorimeter. The skilled artisan is well aware of this principle, methods and instruments to quantify FRET.

Using the FRET assay the inventors compared TaqWT, TaqΔ289, TaqΔ279, and TaqΔ288, whereby each polymerase was recombinantly expressed in *E. coli*. In a lysate of the respective expressing culture, each DNA polymerase was tested for thermostability of DNA polymerase activity. Activity was measured in lysate samples before and after heat incubation at 97° C. for 35 min. It was surprisingly found that due to heat treatment DNA polymerase activity of TaqWT, TaqΔ289, and TaqΔ279 was decreased to less than 50%, with TaqΔ279 retaining activity between about 30% and less than about 50%, TaqΔ289 retaining activity between about 15% and about 30%, and TaqWT retaining activity between 0% and about 5%. In contrast, TaqΔ288 expressed with a terminal methionine retained activity between above about 50% and about 80%.

Using the same FRET activity assay, TaqWT and TaqΔ288 were compared as purified enzymes in a PCR reaction mixture. Following heat incubation at 98° C. for 30 min, TaqWT retained activity between about 10% and about 15%. In contrast, TaqΔ288 retained activity between about 30% and about 35%.

Using the same FRET activity assay, TaqWT, TaqΔ279 and TaqΔ288 were compared as purified enzymes in a stabilized preparation, that is, a storage buffer containing 50% glycerol. TaqWT, TaqΔ279 and TaqΔ288 were kept in the same storage buffer. Following heat incubation at 98° C. for 30 min, TaqWT retained activity between about 40% and about 50%. TaqΔ279 retained activity between about 80% and about 100%. TaqΔ288 retained activity between about 90% and about 100%.

Thermostability of TaqΔ288 with and without N-terminal methionine was indistinguishable.

A first embodiment of the invention is a polypeptide with DNA polymerase activity, characterized in that the amino acid sequence of the polypeptide is the amino acid sequence of *Thermus aquaticus* (Taq) DNA polymerase lacking the N-terminal 288 amino acids of Taq DNA polymerase. In the present text said polypeptide is also referred to as TaqΔ288. Preferably, the amino acid sequence of the polypeptide is the amino acid sequence of SEQ ID NO: 2.

The polypeptide according to the invention can be produced using more than one method. E.g., the polypeptide can be obtained from a transformed host cell which recombinantly expresses the polypeptide. The amino acid sequence of the polypeptide is however governed by the codons of the open reading frame encoding the polypeptide. A functional open reading frame requires a start codon encoding an N-terminal methionine residue. Therefore, in another embodiment of the invention the amino acid sequence of the polypeptide additionally has an N-terminal methionine residue. Preferably, the amino acid sequence of the polypeptide is the amino acid sequence of SEQ ID NO: 4. In the present document the polypeptides of both SEQ ID NO: 2 and SEQ ID NO: 4 are referred to as TaqΔ288.

Preferably, the thermostability of the polypeptide is enhanced when compared to the native enzyme, that is Taq DNA polymerase with the original amino acid sequence (TaqWT) according to SEQ ID NO: 7. It is also preferred that thermostability is enhanced when compared to the deletion fragments TaqΔ289 and TaqΔ279. The inventors have found that when expressing recombinantly and under the same conditions in *E. Coli* TaqΔ288 (with an N-terminal methionine), TaqΔ289, TaqΔ279 and TaqWT, TaqΔ288 has the highest thermostability when compared to the others.

Another embodiment of the invention is a nucleotide sequence encoding a polypeptide according to the invention. Those of skill in the art recognize that a polypeptide with DNA polymerase activity and increased thermostability according to the invention is most easily constructed by recombinant DNA techniques. In a preferred embodiment of the invention the nucleotide sequence is the nucleotide sequence of SEQ ID NO: 1 or SEQ ID NO: 3.

Also, the skilled artisan is aware of silent codon changes (i.e. the amino acid encoded is unchanged) that can be introduced in the nucleotide sequence encoding the first 10 to 20 amino terminal amino acid residues of the polypeptide, and which do not affect the sequence of the polypeptide. Such changes may lead to an optimized nucleotide sequence and may in a transformed host cell such as an *E. coli* cell or in a cell-free expression system such as the cause an increased production of the polypeptide according to the invention. Other optimized nucleotide sequences encoding a polypeptide of the invention can be obtained by introducing silent codon changes in the entire coding sequence. This can be particularly useful if the polypeptide is to be expressed in a prokaryotic host cell of, e.g., the *Bacillus* species or in a eukaryotic host cell such as a yeast cell, preferably a methylotrophic yeast cell.

To construct the expression vector, a DNA is obtained that encodes the polypeptide with DNA polymerase activity according to the invention or a fusion of the polypeptide to an additional sequence that does not destroy activity or to an additional sequence cleavable under controlled conditions (such as treatment with peptidase) to give an active protein. The coding sequence is then placed in operable linkage with suitable control sequences in an expression vector. Thus, another embodiment of the invention is a recombinant DNA vector comprising a DNA sequence according to the invention.

The vector is used to transform a suitable host cell, and the transformed host cell is cultured under conditions suitable for expression of the recombinant polypeptide with DNA polymerase activity. The vector can be designed to replicate autonomously in the host cell or to integrate into the chromosomal DNA of the host cell.

Each of the foregoing steps can be done in a variety of ways. For example, the desired coding sequence may be obtained from genomic fragments and used directly in appropriate hosts. The construction for expression vectors operable in a variety of hosts is made using appropriate replicons and control sequences, as set forth generally below. Construction of suitable vectors containing the desired coding and control sequences employs standard ligation and restriction techniques that are well understood in the art. Isolated plasmids, DNA sequences, or synthesized oligonucleotides are cleaved, modified, and relegated in the form desired. Suitable restriction sites can, if not normally available, be added to the ends of the coding sequence so as to facilitate construction of an expression vector, as exemplified below.

For portions of vectors or coding sequences that require sequence modifications, a variety of site-specific primer-directed mutagenesis methods are available. The polymerase chain reaction (PCR) can be used to perform site-specific mutagenesis. In another technique now standard in the art, a synthetic oligonucleotide encoding the desired mutation is used as a primer to direct synthesis of a complementary nucleic acid sequence of a single-stranded vector, such as pBS 13+, that serves as a template for construction of the extension product of the mutagenizing primer. The mutagenized DNA is transformed into a host bacterium, and cultures of the transformed bacteria are plated and identified. The identification of modified vectors may involve transfer of the DNA of selected transformants to a nitrocellulose filter or other membrane and the "lifts" hybridized with kinased synthetic primer at a temperature that permits hybridization of an exact match to the modified sequence but prevents hybridization with the original strand. Transformants that contain DNA that hybridizes with the probe are then cultured and serve as a reservoir of the modified DNA.

The person skilled in the art is also aware of expression vectors that allow the construction by recombinant means of fusion polypeptides containing a so called "histidine tag". A (poly)histidine tag is an amino acid sequence containing preferably 6 consecutive histidines. The histidine tag is usually fused to the N-terminus or the C-terminus of a desired polypeptide. Purification of such a fusion polypeptide is facilitated by immobilize metal affinity chromatography in which polyhistidine tagged fusion polypeptides are adsorbed by metal ions immobilized on metal-chelating resins. An example therefor is the QIAexpress purification system from Qiagen. The same company provides an expression vector (pQE) that can be used to produce polyhistidine-tagged fusion polypeptides.

The histidine tag is, however, not necessarily desired as being part of the purified polypeptide with DNA activity. To this end, an additional sequence providing a protease cleavage site can be inserted between the histidine tag and the desired polypeptide. A well-known example is a sequence providing a cleavage site for factor X protease. Therefore, another embodiment of the invention is a recombinant DNA vector comprising a DNA sequence according to the invention. Preferably, the DNA sequence encodes a fusion polypeptide consisting of (i) a terminal histidine tag, (ii) an amino acid sequence providing a factor X protease cleavage site adjacent to the histidine tag, and (iii) the polypeptide according to the invention. It is understood that the factor X protease cleavage site in the fusion polypeptide is capable of being recognized and cleaved by a protein with factor X protease activity. More preferred, the DNA sequence encodes a fusion polypeptide which has the amino acid sequence of SEQ ID NO: 5.

When one desires to produce a polypeptide with DNA polymerase activity according to the invention or a derivative thereof such as a fusion polypeptide, the production of a recombinant form of the polypeptide typically involves the construction of an expression vector, that is a recombinant DNA vector, the transformation of a host cell with the vector, and culture of the transformed host cell under conditions such that expression will occur. Thus, another embodiment of the invention is a recombinant host cell transformed with a recombinant DNA vector according to the invention.

The control sequences, recombinant DNA vectors, and transformation methods are dependent on the type of host cell used to express the gene. Generally, prokaryotic, yeast, insect, or mammalian cells are used as hosts. Prokaryotic hosts are in general the most efficient and convenient for the production of recombinant proteins and are therefore preferred for the expression of a polypeptide or a fusion polypeptide of the present invention.

The prokaryote most frequently used to express recombinant proteins is *E. coli*. The skilled artisan is aware of numerous *E. coli* strains and expression systems that can be used to practice the present invention. However, microbial strains other than *E. coli* can also be used, such as bacilli, for example *Bacillus subtilis*, various species of *Pseudomonas*, and other bacterial strains, for recombinant expression of the thermostable DNA polymerases of the present invention. In such prokaryotic systems, plasmid vectors that contain replication sites and control sequences derived from the host or a species compatible with the host are typically used.

In addition to bacteria, eukaryotic microbes, such as yeast, can also be used as recombinant host cells. A polypeptide or a fusion polypeptide according to the invention can therefore also be produced using, preferably, methylotrophic yeast as a eukaryotic microbial host organism. Methylotrophic yeasts have the biochemical pathways necessary for methanol utilization and are classified into four genera, based upon cell morphology and growth characteristics: *Hansenula, Pichia, Candida*, and *Torulopsis*. The most highly developed methylotrophic host systems utilize *Pichia pastoris* (*Komagataella pastoris*) and *Hansenula polymorpha* (*Pichia angusta*). Expression of heterologous proteins in yeast is described in U.S. Pat. Nos. 5,618,676, 5,854,018, 5,856,123, and 5,919,651.

Terminator sequences may also be used to enhance expression when placed at the 3' end of the coding sequence. Such terminators are found in the 3' untranslated region following the coding sequences in yeast-derived genes. Any vector containing a yeast-compatible promoter, origin of replication, and other control sequences is suitable for use in constructing yeast expression vectors for the thermostable DNA polymerases of the present invention.

Moreover, the nucleotide sequences which code for a polypeptide with DNA polymerase activity or a fusion polypeptide containing the same according to the present invention can also be expressed in eukaryotic host cell cultures derived from multicellular organisms.

Depending on the host cell used, transformation is done using standard techniques appropriate to such cells. The calcium treatment employing calcium chloride, as described by Cohen, S. N., et al., Proc. Natl. Acad. Sci. USA 69 (1972) 2110-2114 is used for prokaryotes or other cells that contain substantial cell wall barriers. Infection with *Agrobacterium tumefaciens* (Shaw, C. H., et al., Gene 23 (1983) 315-330) is used for certain plant cells. For mammalian cells, the calcium phosphate precipitation method of Graham and van der Eb, Virology 52 (1978) 546 is preferred. Transformations into yeast are carried out according to the method of van Solingen, P., and Plaat, J. B., J. Bact. 130 (1977) 946-947 and Hsiao, C. L., and Carbon, J., Proc. Natl. Acad. Sci. USA 76 (1979) 3829-3833.

Another embodiment of the invention is a method for producing a polypeptide with DNA polymerase activity, comprising the steps of (a) transforming a host cell with a recombinant DNA vector according to the invention; (b) culturing the host cell and expressing in said host cell the polypeptide with DNA polymerase activity; (c) purifying the polypeptide with DNA polymerase activity expressed in step (b). Purification of the recombinantly expressed polypeptide is achieved similarly as with recombinantly expressed TaqWT (U.S. Pat. No. 5,079,352) or deletion fragments thereof (U.S. Pat. Nos. 5,616,494; 5,436,149), except that TaqΔ288 is obtained. More preferred is a method for producing a polypeptide with DNA polymerase activity, comprising the steps of (a) transforming a host cell with a recombinant DNA vector according to the invention; (b) culturing the host cell and expressing in said host cell a fusion polypeptide consisting of (i) a terminal histidine tag, (ii) an amino acid sequence providing a factor X protease cleavage site adjacent to the histidine tag, and (iii) the polypeptide according to the invention; (c) purifying the fusion polypeptide expressed in step (b); (d) cleaving the fusion polypeptide by way of incubating said fusion polypeptide in the presence of a protease with factor X proteolytic activity, thereby detaching the polypeptide with DNA polymerase activity from the factor X protease cleavage site and the histidine tag; (e) purifying the polypeptide with DNA polymerase activity of step (d). It is even more preferred that in step (c) the fusion polypeptide is purified using a particulate affinity matrix capable of binding a histidine tag. It is even more preferred that in step (d) the histidine tag of the fusion polypeptide is bound to the particulate affinity matrix. It is even more preferred that the particulate affinity matrix is a chromatography material coated with a metal-chelating resin, and metal ions are immobilized on the coated chromatography material. It is even more preferred that the chromatography material is coated with nickel-nitrilotriacetic acid (Ni-NTA). In this regard, the person skilled in the art is aware of EP 1 069 131. Thus, a preferred way of isolating a histidine-tagged fusion polypeptide according to the invention which has been recombinantly expressed in a culture of transformed *E. coli* cells is to prepare a lysate of the cells. One way to prepare a lysate is by suspending the cells in a lysate buffer and treating the cells with ultrasound. The DNA present in the lysate is digested with a DNase, preferred is DNase I. *E. coli* proteins are subsequently degraded by way of heat denaturation (30 min, 72° C. preferred) and can be separated from the lysate by centrifugation. Following centrifugation, the cleared supernatant is chromatographed using a Ni-NTA Superflow column (Qiagen Catalogue No. 30410, 30430, or 30450), whereby the histidine-tagged fusion polypeptide is bound to the immobilized metal affinity matrix of the column. Following two washes with washing buffer, a gradient of washing buffer and elution buffer is applied, whereby the elution buffer gradually replaces the washing buffer in the gradient. Thereby the histidine-tagged fusion polypeptide can be eluted from the column. Further, the eluted fusion polypeptide is incubated in the presence of factor X protease under conditions supporting specific proteolytic activity of factor X protease. Following heat denaturation (30 min, 72° C. preferred) cleaved off histidine-tags and uncleaved fusion polypeptides are separated from the product, that is to say TaqΔ288, by another chromatography using a Ni-NTA Superflow column. The flow-through including the product is collected. Further processing steps may include concentration and dialysis, preferably against a buffer supporting stabilization of TaqΔ288 resulting in a stabilized preparation of the polypeptide according to the invention.

Alternatively, the fusion polypeptide can be cleaved with factor X protease when bound to the immobilized metal affinity matrix of the column. In this case, the column material to which the fusion polypeptide is bound is incubated in the presence of factor X protease under conditions supporting specific proteolytic activity of factor X protease. Subsequent washing with a buffer which is not an elution buffer, i.e. a buffer which supports binding of the histidine tag to the Ni-NTA-coated chromatographic material, will render the TaqΔ288 polypeptide in the flow-through, together with factor X protease. Subsequently, factor X protease is inactivated and the TaqΔ288 polypeptide is purified.

For long-term stability, the thermostable DNA polymerase enzymes of the present invention can be stored in a buffer that contains one or more non-ionic polymeric detergents. Such detergents are generally those that have a molecular weight in the range of approximately 100 to 250,000 daltons, preferably about 4,000 to 200,000 daltons, and stabilize the enzyme at a pH of from about 3.5 to about 9.5, preferably from about 4 to 8.5. Examples of such detergents include those specified on pages 295-298 of McCutcheon's Emulsifiers & Detergents, North American edition (1983), published by the McCutcheon Division of MC Publishing Co., 175 Rock Road, Glen Rock, N.J. (USA).

Preferably, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. More particularly preferred are TWEEN 20, a polyoxyethylated (20) sorbitan monolaurate from ICI Americas Inc., Wilmington, Del., and ICONOL NP-40, an ethoxylated alkyl phenol (nonyl) from BASF Wyandotte Corp., Parsippany, N.J.

Another embodiment of the invention is a stabilized preparation comprising a polypeptide according to the invention in a buffer containing one or more non-ionic polymeric detergents. Preferably, the buffer of the stabilized preparation contains components selected from the group consisting of glycerol, KCl, Tris/HCl (Tris(hydroxymethyl)-aminomethanehydrochloride), EDTA (ethylenediaminetetraacetic acid disodium salt), TWEEN 20, and dithiothreitol (DTT). More preferred is a stabilized preparation consisting of 63% (weight by volume) glycerol, 100 mM KCl, 20 mM Tris/HCl pH 8.5, 0,1 mM EDTA, 0.5% (volume by volume) TWEEN 20, 1 mM DTT.

In each cycle of a PCR amplification, a double-stranded target sequence is denatured, primers are annealed to each strand of the denatured target, and the primers are extended by the action of a DNA polymerase. Specificity of amplification depends on the specificity of primer hybridization. Primers are selected to be complementary to, or substantially complementary to, sequences occurring at the 3' end of each strand of the target nucleic acid sequence. Under the elevated temperatures used in a typical PCR, the primers hybridize only to the intended target sequence. However, amplification reaction mixtures are typically assembled at room temperature, well below the temperature needed to insure primer hybridization specificity. Under such less stringent conditions, the primers may bind non-specifically to other only partially complementary nucleic acid sequences (or even to other primers) and initiate the synthesis of undesired extension products, which can be amplified along with the target sequence. Amplification of the non-specific primer extension products can compete with amplification of the desired target sequences and can significantly decrease the efficiency of the amplification of the desired sequence. Problems caused by non-specific amplification are discussed further in Chou, Q., et al., Nucleic Acids Res. 20 (1992) 1717-1723.

Non-specific amplification can be reduced by reducing the formation of extension products from primers bound to non-target sequences prior to the start of the reaction. In one method, referred to as a "hot-start" protocol, one or more critical reagents are withheld from the reaction mixture until the temperature is raised sufficiently to provide the necessary hybridization specificity. In this manner, the reaction mixture cannot support primer extension during the time that the reaction conditions do not insure specific primer hybridization.

As a frequent feature in "hot start" protocols, the DNA polymerase activity is withheld from PCR reaction mixtures by way of reversible inactivation of the DNA polymerase, that is to say, reversibly blocked DNA polymerase. One method uses a chemically modified DNA polymerase that becomes active only after incubation of the DNA polymerase for a certain period of time at elevated temperature, thus preventing production of unwanted DNA synthesis products during set-up of the PCR reaction mixture. U.S. Pat. No. 6,183,998 describes the reversible inactivation of thermostable DNA using an aldehyde such as formaldehyde. Essentially complete inactivation of the enzyme at ambient temperatures is achieved, with recovery of enzymatic activity at temperatures above 50° C. The patents EP 0 771 870 and U.S. Pat. No. 6,479,264 describe the reversible inactivation of thermostable DNA polymerase using a dicarboxylic acid anhydride. U.S. Pat. Nos. 5,773,258 and 5,677,152 describe the reversible inactivation of enzymatic activity of a thermostable enzyme. Preferred reagents for covalent modification include maleic anhydride; substituted maleic anhydrides such as citraconic anhydride, cis-aconitic anhydride, and 2,3-dimethylmaleic anhydride; exo-cis-3,6-endoxo-delta 4-tetrahydrophthalic anhydride; and 3,4,5,6-tetrahydrophthalic anhydride. Accordingly, citraconic anhydride and cis-aconitic anhydride are preferred for the preparation of reversibly blocked DNA polymerases for use in PCR amplifications. The reversibly inactivated enzyme is the result of a chemical modification of the protein which inactivates the enzyme. The activity of the inactivated enzyme is recovered by an incubation of the reaction mixture at an elevated temperature prior to, or as part of, the amplification reaction. Thus, in another preferred embodiment of the invention, the polypeptide according to the present invention is covalently coupled to a compound capable of reversibly blocking the DNA polymerase activity of the polypeptide when coupled covalently to said polypeptide. It is more preferred that the compound is selected from the group consisting of (a) citraconic anhydride, (b) cis-aconitic anhydride, (c) 2,3-dimethylmaleic anhydride, (d) exo-cis-3,6-endoxo-delta 4-tetrahydrophthalic anhydride, and (e) 3,4,5,6-tetrahydrophthalic anhydride.

Another preferred embodiment of the invention is a stabilized preparation comprising a polypeptide with DNA polymerase activity, whereby the polypeptide is covalently coupled to a compound capable of reversibly blocking the DNA polymerase activity of the polypeptide when coupled covalently to said polypeptide. It is more preferred that the compound is selected from the group consisting of (a) citraconic anhydride, (b) cis-aconitic anhydride, (c) 2,3-dimethylmaleic anhydride, (d) exo-cis-3,6-endoxo-delta 4-tetrahydrophthalic anhydride, and (e) 3,4,5,6-tetrahydrophthalic anhydride.

Yet, another preferred embodiment of the invention is a stabilized preparation comprising a polypeptide with DNA polymerase activity, whereby the polypeptide is bound by an antibody capable of reversibly blocking the DNA polymerase activity of the polypeptide when binding said polypeptide. DNA polymerase activity can also be blocked reversibly by a non-covalent modification of the DNA polymerase. U.S. Pat. No. 5,338,671 discloses the use of antibodies specific for the DNA polymerase enzyme to inhibit the DNA polymerase activity. Pre-mixing of DNA polymerase and DNA polymerase-specific antibodies results in the formation of an antibody-polymerase complex. Under these conditions substantially no oligonucleotide extension activity can be detected. At elevated temperatures, the antibody dissociates from the complex, thus releasing the DNA polymerase, which can then function in DNA synthesis during the PCR. Preferably, the antibody is a monoclonal antibody against Taq DNA polymerase. Monoclonal antibodies against Taq DNA polymerase are known in the art and described, for example, in U.S. Pat. No. 5,338,671. Preferably, the monoclonal antibodies against Taq DNA polymerase are TP4-9.2 and TP1-12.2, obtainable from hybridomas deposited with the American Type Culture Collection (ATCC), and designated by ATCC Accession Numbers HB11807 and HB 11127, respectively. Preferred antibodies have an association constant for the polymerase of at least about $1 \times 10^7$ $M^{-1}$. In accordance with the present invention antibodies defined as specific to the DNA polymerase are those antibodies that are capable of inhibiting the enzymatic activity of the DNA polymerase at temperatures from about 20-40° C. The antibodies of the invention are either inactivated by elevated temperatures used during PCR thermal cycling or by pre-incubating a PCR reaction mixture at an elevated temperature before starting thermal cycling. The ability of the antibodies to inhibit enzymatic activity of the polymerase can be determined by assays known to one of ordinary skill in the art, as described, for example, by Sharkey, D. J., et al., BioTechnology 12 (1994) 506-509. For example, standard assays for the enzymatic activity of DNA polymerases may be based upon the ability of the polymerase to incorporate 3H-dNTP in single strand gaps made in DNA. The ability of an antibody to inhibit polymerase activity is determined by preincubating antibody with the polymerase and then conducting the standard polymerase assay. Antibodies capable of significantly decreasing polymerase activity in such an assay are useful in the present invention. Similar assays may be used to determine that the desired antibodies are inactivated by heat. Briefly, the assay for the ability of the antibody to inhibit the polymerase is modified by raising to the desired temperature, followed by cooling and assaying for polymerase activity. The desired antibodies are inactivated by temperatures of 85-95° C., thus releasing active polymerase.

Another embodiment of the invention is use of a polypeptide according to the invention, the polypeptide according to the invention covalently coupled to a compound capable of reversibly blocking the DNA polymerase activity of the polypeptide when coupled covalently to said polypeptide, the polypeptide according to the invention bound by an antibody capable of reversibly blocking the DNA polymerase activity of the polypeptide when binding said polypeptide, or a stabilized preparation according to the invention, for producing primer extension products. Primer extension products are produced, e.g., when performing PCR or a sequencing reaction using the Sanger method. Thus preferred is the use according to the invention for sequencing a nucleic acid template. Also preferred is the use according to the invention for amplifying a target nucleic acid. Another example for primer extension is nick translation. The skilled artisan is aware of a number of other examples illustrating the term "producing primer extension products". The invention encompasses producing primer extension products using a polypeptide with DNA polymerase activity according to the invention or a preparation containing the same.

Another embodiment of the invention is a kit for producing primer extension products comprising a stabilized preparation according to any of the invention. Preferred is a kit for sequencing a nucleic acid template. Also preferred is a kit for amplifying a target nucleic acid. Very much preferred is a kit for amplifying a target nucleic acid using the LightCycler. An example therefor is the LightCycler DNA Master SYBR Green I kit (Roche Diagnostics GmbH, Mannheim; Catalogue No. 2015099). Accordingly, such a kit may comprise three vials, one of these (1) containing a 10× concentrated reaction mix, containing a stabilized preparation of TaqΔ288 or TaqΔ288 with reversibly blocked DNA polymerase activity, and additionally dNTP mix, optionally with dUTP instead of dTTP, SYBR green I dye, and 10 mM $MgCl_2$. Another vial of the kit (2) contains a stock solution of $MgCl_2$ at a concentration of, e.g., 25 mM. Another vial of the kit (3) contains sterile and PCR grade purified water to adjust the final reaction volume.

Another embodiment of the invention is a method for amplifying a target nucleic acid in a sample, comprising the steps of (a) contacting said sample with an amplification reaction mixture containing a primer complementary to said target nucleic acid and a polypeptide selected from the group consisting of (i) a polypeptide according to the invention, (ii) a polypeptide according to the invention covalently coupled to a compound capable of reversibly blocking the DNA polymerase activity of the polypeptide when coupled covalently to said polypeptide, and (iii) a polypeptide according to the invention bound by an antibody capable of reversibly blocking the DNA polymerase activity of the polypeptide when binding said polypeptide, (b) optionally releasing blocked DNA polymerase activity by heat treatment, (c) annealing in the resulting mixture of step (a) said primer to said target nucleic acid, (d) amplifying the target nucleic acid by incubating after step (b) the mixture to allow formation of primer extension products.

For ease of discussion, the protocol set forth below assumes that the specific sequence to be amplified is contained in a double-stranded nucleic acid. However, the process is equally useful in amplifying single-stranded nucleic acid, such as mRNA, although in the preferred embodiment the ultimate product is still double-stranded DNA. In the amplification of a single-stranded nucleic acid, the first step involves the synthesis of a complementary strand (one of the two amplification primers can be used for this purpose), and the succeeding steps proceed as in the double-stranded amplification process described below.

Thus, an exemplary amplification process comprises the steps of: (a) contacting each nucleic acid strand with four different nucleoside triphosphates and two oligonucleotide primers for each specific sequence being amplified, wherein each primer is selected to be substantially complementary to the different strands of the specific sequence, such that the extension product synthesized from one primer, when separated from its complement, can serve as a template for synthesis of the extension product of the other primer, said contacting being at a temperature that allows hybridization of each primer to a complementary nucleic acid strand; (b) contacting each nucleic acid strand, at the same time as or after step (a), with a polypeptide with DNA polymerase activity according to the present invention that enables combination of the nucleoside triphosphates to form primer extension products complementary to each strand of the specific nucleic acid sequence; (c) maintaining the mixture from step (b) at an effective temperature for an effective time to promote the activity of the polypeptide with DNA polymerase activity and to synthesize, for each different sequence being amplified, an extension product of each primer that is complementary to each nucleic acid strand template, but not so high as to separate each extension product from the complementary strand template; (d) heating the mixture from step (c) for an effective time and at an effective temperature to separate the primer extension products from the templates on which they were synthesized to produce single-stranded molecules but not so high as to denature irreversibly the enzyme; (e) cooling the mixture from step (d) for an effective time and to an effective temperature to promote hybridization of a primer to each of the single-stranded molecules produced in step (d); and (f) maintaining the mixture from step (e) at an effective temperature for an effective time to promote the activity of the polypeptide with DNA polymerase activity and to synthesize, for each different sequence being amplified, an extension product of each primer that is complementary to each nucleic acid template produced in step (d) but not so high as to separate each extension product from the complementary strand template. The effective times and temperatures in steps (e) and (f) may coincide, so that steps (e) and (f) can be carried out simultaneously. Steps (d)-(f) are repeated until the desired level of amplification is obtained.

The amplification method is useful not only for producing large amounts of a specific nucleic acid sequence of known sequence but also for producing nucleic acid sequences that are known to exist but are not completely specified. One need know only a sufficient number of bases at both ends of the sequence in sufficient detail so that two oligonucleotide primers can be prepared that will hybridize to different strands of the desired sequence at relative positions along the sequence such that an extension product synthesized from one primer, when separated from the template (complement), can serve as a template for extension of the other primer into a nucleic acid sequence of defined length. The greater the knowledge about the bases at both ends of the sequence, the greater can be the specificity of the primers for the target nucleic acid sequence and the efficiency of the process and specificity of the reaction.

In any case, an initial copy of the sequence to be amplified must be available, although the sequence need not be pure or a discrete molecule. In general, the amplification process involves a chain reaction for producing, in exponential quantities relative to the number of reaction steps involved, at least one specific nucleic acid sequence given that (a) the ends of the required sequence are known in sufficient detail that oligonucleotides can be synthesized that will hybridize to them and (b) that a small amount of the sequence is available to initiate the chain reaction. The product of the chain reaction will be a discrete nucleic acid duplex with termini corresponding to the 5' ends of the specific primers employed.

Any nucleic acid sequence, in purified or nonpurified form, can be utilized as the starting nucleic acid(s), provided it contains or is suspected to contain the specific nucleic acid sequence one desires to amplify. The nucleic acid to be amplified can be obtained from any source, for example, from plasmids such as pBR322, from cloned DNA or RNA, or from natural DNA or RNA from any source, including bacteria, yeast, viruses, organelles, and higher organisms such as plants and animals. DNA or RNA may be extracted from blood, tissue material such as chorionic villi, or amniotic cells by a variety of techniques. See, e.g., Maniatis et al., Molecular Cloning: A Laboratory Manual, Cold Spring Harbor Laboratory, Cold Spring Harbor, N.Y., 1982, pp. 280-281. Thus, the process may employ, for example, DNA or RNA, including messenger RNA, which DNA or RNA may be single-stranded or double-stranded. In addition, a DNA-RNA hybrid that contains one strand of each may be utilized. A mixture of any of these nucleic acids can also be employed as can nucleic acids produced from a previous amplification reaction (using the same or different primers). The specific nucleic acid sequence to be amplified can be only a fraction of a large molecule or can be present initially as a discrete molecule, so that the specific sequence constitutes the entire nucleic acid.

The sequence to be amplified need not be present initially in a pure form; the sequence can be a minor fraction of a complex mixture, such as a portion of the β-globin gene contained in whole human DNA (as exemplified in Saiki, R. K., et al., Science 230 (1985) 1350-1354) or a portion of a nucleic acid sequence due to a particular microorganism, which organism might constitute only a very minor fraction of a particular biological sample. The cells can be directly used in the amplification process after suspension in hypotonic buffer and heat treatment at about 90° C.-100° C. until cell lysis and dispersion of intracellular components occur (generally 1 to 15 minutes). After the heating step, the amplification reagents may be added directly to the lysed cells. The starting nucleic acid sequence can contain more than one desired specific nucleic acid sequence. The amplification process is useful not only for producing large amounts of one specific nucleic acid sequence but also for amplifying simultaneously more than one different specific nucleic acid sequence located on the same or different nucleic acid molecules.

Primers play a key role in the PCR process. The word "primer" as used in describing the amplification process can refer to more than one primer, particularly in the case where there is some ambiguity in the information regarding the terminal sequence(s) of the fragment to be amplified or where one employs the degenerate primer process described in WO 91/05753. For instance, in the case where a nucleic acid sequence is inferred from protein sequence information, a collection of primers containing sequences representing all possible codon variations based on degeneracy of the genetic code can be used for each strand. One primer from this collection will be sufficiently homologous with a portion of the desired sequence to be amplified so as to be useful for amplification.

In addition, more than one specific nucleic acid sequence can be amplified from the first nucleic acid or mixture of nucleic acids, so long as the appropriate number of different oligonucleotide primers are utilized. For example, if two different specific nucleic acid sequences are to be produced, four primers are utilized. Two of the primers are specific for one of the specific nucleic acid sequences, and the other two primers are specific for the second specific nucleic acid sequence. In this manner, each of the two different specific sequences can be produced exponentially by the present process.

A sequence within a given sequence can be amplified after a given number of amplification cycles to obtain greater specificity in the reaction by adding, after at least one cycle of amplification, a set of primers that are complementary to internal sequences (i.e., sequences that are not on the ends) of the sequence to be amplified. Such primers can be added at any stage and will provide a shorter amplified fragment. Alternatively, a longer fragment can be prepared by using primers with non-complementary ends but having some overlap with the primers previously utilized in the amplification.

Primers also play a key role when the amplification process is used for in vitro mutagenesis. The product of an amplification reaction where the primers employed are not exactly complementary to the original template will contain the sequence of the primer rather than the template, so introducing an in vitro mutation. In further cycles, this mutation will be amplified with an undiminished efficiency because no further mispaired priming is required. The process of making an altered DNA sequence as described above could be repeated on the altered DNA using different primers to induce further sequence changes. In this way, a series of mutated sequences can gradually be produced wherein each new addition to the series differs from the last in a minor way, but from the original DNA source sequence in an increasingly major way.

Because the primer can contain as part of its sequence a non-complementary sequence, provided that a sufficient amount of the primer contains a sequence that is complementary to the strand to be amplified, many other advantages can be realized. For example, a nucleotide sequence that is not complementary to the template sequence (such as, e.g., a promoter, linker, coding sequence, etc.) may be attached at the 5' end of one or both of the primers and so appended to the product of the amplification process. After the extension primer is added, sufficient cycles are run to achieve the desired amount of new template containing the non-complementary nucleotide insert. This allows production of large quantities of the combined fragments in a relatively short period of time (e.g., two hours or less) using a simple technique.

Oligonucleotide primers can be prepared using any suitable method, such as, for example, the phosphotriester and phosphodiester methods described above, or automated embodiments thereof. In one such automated embodiment, diethylphosphoramidites are used as starting materials and can be synthesized as described by Beaucage et al., Tetrahedron Letters 22 (1981) 1859-1862. One method for synthesizing oligonucleotides on a modified solid support is described in U.S. Pat. No. 4,458,066. One can also use a primer that has been isolated from a biological source (such as a restriction endonuclease digest).

No matter what primers are used, however, the reaction mixture must contain a template for PCR to occur, because the specific nucleic acid sequence is produced by using a nucleic acid containing that sequence as a template. The first step involves contacting each nucleic acid strand with four different nucleoside triphosphates and two oligonucleotide primers for each specific nucleic acid sequence being amplified or detected. If the nucleic acids to be amplified or detected are DNA, then the nucleoside triphosphates are usually dATP, dCTP, dGTP, and dTTP, although various nucleotide derivatives can also be used in the process. For example, when using PCR for the detection of a known sequence in a sample of unknown sequences, dTTP is often replaced by dUTP in order to reduce contamination between samples as taught in WO 91/05210.

The concentration of nucleoside triphosphates can vary widely. Typically, the concentration is 50 to 500 μM of each dNTP in the buffer for amplification, and $MgCl_2$ is present in the buffer in an amount of 1 to 3 mM to activate the polymerase and increase the specificity of the reaction. However, dNTP concentrations of 1 to 20 pM may be preferred for some applications, such as DNA sequencing or generating radiolabeled probes at high specific activity.

The nucleic acid strands of the target nucleic acid serve as templates for the synthesis of additional nucleic acid strands, which are extension products of the primers. This synthesis can be performed using any suitable method, but generally occurs in a buffered aqueous solution, preferably at a pH of 7 to 9, most preferably about 8. To facilitate synthesis, a molar excess of the two oligonucleotide primers is added to the buffer containing the template strands. As a practical matter, the amount of primer added will generally be in molar excess over the amount of complementary strand (template) when the sequence to be amplified is contained in a mixture of complicated long-chain nucleic acid strands. A large molar excess is preferred to improve the efficiency of the process. Accordingly, primer:template ratios of at least 1000:1 or higher are generally employed for cloned DNA templates, and primer:template ratios of about 100:1 or higher are generally employed for amplification from complex genomic samples.

The mixture of template, primers, and nucleoside triphosphates is then treated according to whether the nucleic acids being amplified or detected are double- or single-stranded. If the nucleic acids are single-stranded, then no denaturation step need be employed prior to the first extension cycle, and the reaction mixture is held at a temperature that promotes hybridization of the primer to its complementary target (template) sequence. Such temperature is generally from about 35° C. to 65° C. or more, preferably about 37° C. to 60° C. for an effective time, generally from a few seconds to five minutes, preferably from 30 seconds to one minute. A hybridization temperature of 35° C. to 70° C. may be used. Primers that are 15 nucleotides or longer in length are used to increase the specificity of primer hybridization. Shorter primers require lower hybridization temperatures.

The complement to the original single-stranded nucleic acids can be synthesized by adding a polypeptide with DNA polymerase activity according to the invention in the presence of the appropriate buffer, dNTP's, and one or more oligonucleotide primers. If an appropriate single primer is added, the primer extension product will be complementary to the single-stranded nucleic acid and will be hybridized with the nucleic acid strand in a duplex of strands of equal or unequal length (depending on where the primer hybridizes to the template), which may then be separated into single strands as described above to produce two single, separated, complementary strands. A second primer would then be added so that subsequent cycles of primer extension would occur using both the original single-stranded nucleic acid and the extension product of the first primer as templates. Alternatively, two or more appropriate primers (one of which will prime synthesis using the extension product of the other primer as a template) can be added to the single-stranded nucleic acid and the reaction carried out.

If the nucleic acid contains two strands, as in the case of amplification of a double-stranded target or second-cycle amplification of a single-stranded target, the strands of nucleic acid must be separated before the primers are hybridized. This strand separation can be accomplished by any suitable denaturing method, including physical, chemical or enzymatic means. One preferred physical method of separating the strands of the nucleic acid involves heating the nucleic acid until complete (>99%) denaturation occurs. Typical heat denaturation involves temperatures ranging from about 80° C. to 105° C. for times generally ranging from about a few seconds to minutes, depending on the composition and size of the nucleic acid. Preferably, the effective denaturing temperature is 90° C.-100° C. for a few seconds to 1 minute. Strand separation may also be induced by an enzyme from the class of enzymes known as helicases or the enzyme RecA, which has helicase activity and in the presence of ATP is known to denature DNA. The reaction conditions suitable for separating the strands of nucleic acids with helicases are described by Kuhn Hoffmann-Berling, CSH-Quantitative Biology 43 (1978) 63, and techniques for using RecA are reviewed in Radding, C. M., Ann. Rev. Genetics 16 (1982) 405-437. The denaturation produces two separated complementary strands of equal or unequal length.

If the double-stranded nucleic acid is denatured by heat, the reaction mixture is allowed to cool to a temperature that promotes hybridization of each primer to the complementary target (template) sequence. This temperature is usually from about 35° C. to 65° C. or more, depending on reagents, preferably 37° C. to 60° C. The hybridization temperature is maintained for an effective time, generally a few seconds to minutes, and preferably 10 seconds to 1 minute. In practical terms, the temperature is simply lowered from about 95° C. to as low as 37° C., and hybridization occurs at a temperature within this range.

Whether the nucleic acid is single- or double-stranded, a polypeptide with DNA polymerase activity according to the invention can be added prior to or during the denaturation step or when the temperature is being reduced to or is in the range for promoting hybridization. Although the thermostability of the polymerases of the invention allows one to add such polymerases to the reaction mixture at any time, one can substantially inhibit non-specific amplification by adding the polymerase to the reaction mixture at a point in time when the mixture will not be cooled below the stringent hybridization temperature. After hybridization, the reaction mixture is then heated to or maintained at a temperature at which the activity of the polypeptide with DNA polymerase activity is promoted or optimized, i.e., a temperature sufficient to increase the activity of the polypeptide with DNA polymerase activity in facilitating synthesis of the primer extension products from the hybridized primer and template. The temperature must actually be sufficient to synthesize an extension product of each primer that is complementary to each nucleic acid template, but must not be so high as to denature each extension product from its complementary template (i.e., the temperature is generally less than about 80° C. to 90° C.).

Depending on the nucleic acid(s) employed, the typical temperature effective for this synthesis reaction generally ranges from about 40° C. to 80° C., preferably 50° C. to 75° C. The temperature more preferably ranges from about 65° C. to 75° C. for the polypeptide with DNA polymerase activity of the present invention. The period of time required for this synthesis may range from about 10 seconds to several minutes or more, depending mainly on the temperature, the length of the nucleic acid, the enzyme, and the complexity of the nucleic acid mixture. The extension time is usually about 30 seconds to a few minutes. If the nucleic acid is longer, a longer time period is generally required for complementary strand synthesis.

The newly synthesized strand and the complement nucleic acid strand form a double-stranded molecule that is used in the succeeding steps of the amplification process. In the next step, the strands of the double-stranded molecule are separated by heat denaturation at a temperature and for a time effective to denature the molecule, but not at a temperature and for a period so long that the polypeptide with DNA polymerase activity is completely and irreversibly denatured or inactivated. After this denaturation of template, the temperature is decreased to a level that promotes hybridization of the primer to the complementary single-stranded molecule (template) produced from the previous step, as described above.

After this hybridization step, or concurrently with the hybridization step, the temperature is adjusted to a temperature that is effective to promote the activity of the polypeptide with DNA polymerase activity to enable synthesis of a primer extension product using as a template both the newly synthesized and the original strands. The temperature again must not be so high as to separate (denature) the extension product from its template, as described above. Hybridization may occur during this step, so that the previous step of cooling after denaturation is not required. In such a case, using simultaneous steps, the preferred temperature range is 50° C. to 70° C.

The heating and cooling steps involved in one cycle of strand separation, hybridization, and extension product synthesis can be repeated as many times as needed to produce the desired quantity of the specific nucleic acid sequence. The only limitation is the amount of the primers, the polypeptide with DNA polymerase activity, and the nucleoside triphosphates present. Usually, from 15 to 30 cycles are completed. For diagnostic detection of amplified DNA, the number of cycles will depend on the nature of the sample, the initial target concentration in the sample and the sensitivity of the detection process used after amplification. For a given sensitivity of detection, fewer cycles will be required if the sample being amplified is pure and the initial target concentration is high. If the sample is a complex mixture of nucleic acids and the initial target concentration is low, more cycles will be required to amplify the signal sufficiently for detection. For general amplification and detection, the process is repeated about 15 times. When amplification is used to generate sequences to be detected with labeled sequence-specific probes and when human genomic DNA is the target of amplification, the process is repeated 15 to 30 times to amplify the sequence sufficiently so that a clearly detectable signal is produced, i.e., so that background noise does not interfere with detection.

No additional nucleotides, primers, or polypeptide with DNA polymerase activity need be added after the initial addition, provided that no key reagent has been exhausted and that the polypeptide with DNA polymerase activity has not become denatured or irreversibly inactivated, in which case additional polymerase or other reagent would have to be added for the reaction to continue. After the appropriate number of cycles has been completed to produce the desired amount of the specific nucleic acid sequence, the reaction can be halted in the usual manner, e.g., by inactivating the polypeptide with DNA polymerase activity by adding EDTA, phenol, SDS, or CHCl3 or by separating the components of the reaction.

The amplification process can be conducted continuously. In one embodiment of an automated process, the reaction mixture can be temperature cycled such that the temperature is programmed to be controlled at a certain level for a certain time. One such instrument for this purpose is the automated machine for handling the amplification reaction developed and marketed by Perkin-Elmer Cetus Instruments. Detailed instructions for carrying out PCR with the instrument are available upon purchase of the instrument. Another example for such an instrument is the LightCycler available from Roche Diagnostics GmbH, Mannheim, Germany.

The polypeptide with DNA polymerase activity of the present invention is very useful in the diverse processes in which amplification of a nucleic acid sequence by PCR is useful. The amplification method may be utilized to clone a particular nucleic acid sequence for insertion into a suitable expression vector, as described in U.S. Pat. No. 4,800,159. The vector may be used to transform an appropriate host cell to produce the gene product of the sequence by standard methods of recombinant DNA technology. Such cloning may involve direct ligation into a vector using blunt-end ligation, or use of restriction enzymes to cleave at sites contained within the primers. Other processes suitable for the thermostable DNA polymerases of the present invention include those described in U.S. Pat. Nos. 4,683,195 and 4,683,202 and EP 0 229 701; EP 0 237 362; and EP 0 258 017. In addition, the present enzyme is useful in asymmetric PCR (see Gyllensten, U. B., and Erlich, H. A., Proc. Natl. Acad. Sci. USA 85 (1988) 7652-7656); inverse PCR (Ochman, H., et al., Genetics 120 (1988) 621-623); and for DNA sequencing (see Innis, M. A., et al., Proc. Natl. Acad. Sci. USA 85 (1988) 9436-9440, and McConlogue, L., et al., Nucleic Acids Res. 16 (1988) 9869), random amplification of cDNA ends (RACE), random priming PCR which is used to amplify a series of DNA fragments, and PCR processes with single sided specificity such as anchor PCR and ligation-mediated anchor PCR as described by Loh, E., in METHODS: A Companion to Methods in Enzymology (1991) 2, pp. 11-19.

Particularly, the polypeptide with DNA polymerase activity according to the invention is useful for amplifying a target nucleic acid using the LightCycler. The LightCycler apparatus as well as protocols for performing PCR are described in the manual "LightCycler Operator's Manual Version 3.5" (October 2000) available from Roche Diagnostics GmbH, Mannheim, Germany. Accordingly, the recommendations given in chapter 4.3.1 likewise apply to TaqΔ288.

Another embodiment of the invention is a method for sequencing a nucleic acid, comprising the step of generating chain-terminated fragments from the nucleic acid template to be sequenced with a polypeptide according to the invention, in the presence of at least one chain terminating agent and one or more nucleotide triphosphates, and determining the sequence of said nucleic acid from the sizes of said fragments.

DNA sequencing by the Sanger dideoxynucleotide method (Sanger, F., et al., Proc. Natl. Acad. Sci. USA 74 (1977) 5463-5467) has undergone significant refinement in recent years, including the development of novel vectors (Yanisch-Perron, C., et al., Gene 33 (1985) 103-119), base analogs (Mills, D. R., and Kramer, F. R., Proc. Natl. Acad. Sci. USA 76 (1979) 2232-2235, and Barr et al., BioTechniques 4 (1986) 428-432), enzymes (Tabor, S., and Richardson, C. C., Proc. Natl. Acad. Sci. USA 84 (1987) 4767-4771, and Innis, M. A., et al., Proc. Natl. Acad. Sci. USA 85 (1988) 9436-9440), and instruments for partial automation of DNA sequence analysis (Smith, L. M., et al., Nature 321 (1986) 674-679; Prober, J. M., et al., Science 238 (1987) 336-341; and Ansorge, W., et al., Nuc. Acids Res. 15 (1987) 4593-4602). The basic dideoxy sequencing procedure involves (i) annealing an oligonucleotide primer to a suitable single or denatured double stranded DNA template; (ii) extending the primer with DNA polymerase in four separate reactions, each containing one α-labeled dNTP or ddNTP (alternatively, a labeled primer can be used), a mixture of unlabeled dNTP's, and one chain-terminating dideoxynucleotide-5'-triphosphate (ddNTP); (iii) resolving the four sets of reaction products on a high-resolution polyacrylamide-urea gel; and (iv) producing an autoradiographic image of the gel that can be examined to infer the DNA sequence. Alternatively, fluorescently labeled primers or nucleotides can be used to identify the reaction products. Known dideoxy sequencing methods utilize a DNA polymerase such as the Klenow fragment of E. Coli DNA polymerase I, reverse transcriptase, Taq DNA polymerase, or a modified T7 DNA polymerase.

As an alternative to basic dideoxy sequencing, cycle dideoxy sequencing is a linear, asymmetric amplification of target sequences in the presence of dideoxy chain terminators. A single cycle produces a family of extension products of all possible lengths. Following denaturation of the extension reaction product from the DNA template, multiple cycles of primer annealing and primer extension occur in the presence of dideoxy terminators. The process is distinct from PCR in that only one primer is used, the growth of the sequencing reaction products in each cycle is linear, and the amplification products are heterogeneous in length and do not serve as template for the next reaction. Cycle dideoxy sequencing is a technique providing advantages for laboratories using automated DNA sequencing instruments and for other high volume sequencing laboratories. It is possible to directly sequence genomic DNA, without cloning, due to the specificity of the technique and the increased amount of signal generated. Cycle sequencing protocols accommodate single and double stranded templates, including genomic, cloned, and PCR-amplified templates.

DNA polymerases with enhanced thermostability, particularly TaqΔ288, have several advantages in cycle sequencing: they tolerate the stringent annealing temperatures which are required for specific hybridization of primer to genomic targets as well as tolerating the multiple cycles of high temperature denaturation which occur in each cycle. Performing the extension reaction at high temperatures, i.e., 70-75° C., results in a significant improvement in sequencing results with DNA that contains secondary structure, due to the destabilization of secondary structure. However, such temperatures will not eliminate all secondary structure.

The following examples, references, tables, sequence listing, and figures are provided to aid the understanding of the present invention, the true scope of which is set forth in the appended claims. It is understood that modifications can be made in the procedures set forth without departing from the spirit of the invention.

REFERENCES

Ansorge, W., et al., Nuc. Acids Res. 15 (1987) 4593-4602
Barr et al., BioTechniques 4 (1986) 428-432
Beaucage et al., Tetrahedron Letters 22 (1981) 1859-1862
Bessman et al., J. Biol. Chem. 223 (1957) 171-177
Buttin, G., and Kornberg, A., J. Biol. Chem. 241 (1966) 5419-5427
Chien et al., Chemical Abstract 85, No. 155559t (1976)
Chou, Q., et al., Nucleic Acids Res. 20 (1992) 1717-1723
Cohen, S. N., et al., Proc. Natl. Acad. Sci. USA 69 (1972) 2110-2114
EP 0 229 701
EP 0 237 362
EP 0 258 017
EP 0 771 870
EP 1 069 131
Graham and van der Eb, Virology 52 (1978) 546
Gyllensten, U. B., and Erlich, H. A., Proc. Natl. Acad. Sci. USA 85 (1988) 7652-7656
Hsiao, C. L., and Carbon, J., Proc. Natl. Acad. Sci. USA 76 (1979) 3829-3833
Innis, M. A., et al., Proc. Natl. Acad. Sci. USA 85 (1988) 9436-9440
Kaledin et al., Chemical Abstract 93, No. 40169p (1989)
Kuhn Hoffmann-Berling, CSH-Quantitative Biology 43 (1978) 63
Lawyer, F. C., et al., J. Biol. Chem. 264 (1989) 6427-6437
Loh, E., in METHODS: A Companion to Methods in Enzymology (1991) 2, pp. 11-19
Maniatis et al., Molecular Cloning: A Laboratory Manual, Cold Spring Harbor Laboratory, Cold Spring Harbor, N.Y., 1982, pp. 280-281
McConlogue, L., et al., Nucleic Acids Res. 16 (1988) 9869
McCutcheon's Emulsifiers & Detergents, North American edition (1983), McCutcheon Division of MC Publishing Co., 175 Rock Road, Glen Rock, N.J. (USA), pp. 295-298
Mills, D. R., and Kramer, F. R., Proc. Natl. Acad. Sci. USA 76 (1979) 2232-2235
Ochman, H., et al., Genetics 120 (1988) 621-623
Prober, J. M., et al., Science 238 (1987) 336-341
Radding, C. M., Ann. Rev. Genetics 16 (1982) 405-437
Saiki, R. K., et al., Science 230 (1985) 1350-1354
Sanger, F., et al., Proc. Natl. Acad. Sci. USA 74 (1977) 5463-5467
Sharkey, D. J., et al., BioTechnology 12 (1994) 506-509
Shaw, C. H., et al., Gene 23 (1983) 315-330
Smith, L. M., et al., Nature 321 (1986) 674-679
Tabor, S., and Richardson, C. C., Proc. Natl. Acad. Sci. USA 84 (1987) 4767-4771
U.S. Pat. No. 4,458,066
U.S. Pat. No. 4,683,195
U.S. Pat. No. 4,683,202
U.S. Pat. No. 4,889,818
U.S. Pat. No. 4,965,188
U.S. Pat. No. 5,079,352
U.S. Pat. No. 5,338,671
U.S. Pat. No. 5,436,149
U.S. Pat. No. 5,616,494
U.S. Pat. No. 5,618,676
U.S. Pat. No. 5,677,152
U.S. Pat. No. 5,773,258
U.S. Pat. No. 5,854,018
U.S. Pat. No. 5,856,123
U.S. Pat. No. 5,885,813
U.S. Pat. No. 5,919,651
U.S. Pat. No. 6,183,998
U.S. Pat. No. 6,479,264
van Solingen, P., and Plaat, J. B., J. Bact. 130 (1977) 946-947
WO 91/02090
WO 91/05210
WO 91/05753
Yanisch-Perron, C., et al., Gene 33 (1985) 103-119

Figure 1:
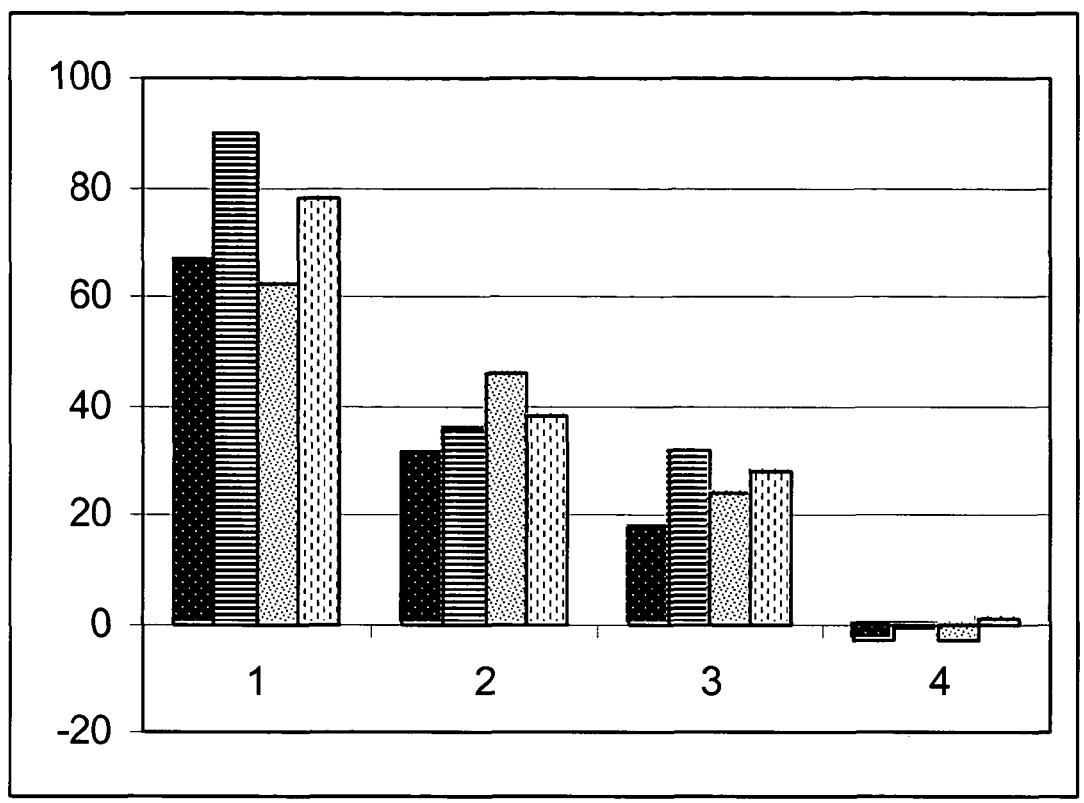
FIG. 1 is a comparison of four experiments to determine the relative activities of TaqΔ288 (1), TaqΔ279 (2), TaqΔ289

(3) and TaqWT (4). Bars corresponding to the same experiment are indicated by a common filling pattern. The bars represent the numerical values given in Table 1.

SPECIFIC EMBODIMENTS

EXAMPLE 1

Construction and Production of the Deletion Mutant TaqΔ288

Starting with the DNA sequence encoding, TaqWT of SEQ ID NO: 6, an oligonucleotide primer including the DNA sequence encoding the sequence MRGS-6xHis-IEGR (SEQ ID NO: 9) and an oligonucleotide primer hybridizing to the DNA sequence coding for the C-terminus of TaqWT a DNA encoding the amino acid sequence of SEQ ID NO: 5 is generated using PCR. The construct is inserted into the pQE80L expression vector.

EXAMPLE 2

Activity of WT Taq Polymerase and N-Terminal Deletion Variants of Taq Polymerase in Bacterial Lysates Using the expression vector pQE80L (Qiagen catalogue no. 32923) the reading frames of TaqWT, TaqΔ279, TaqΔ288, and TaqΔ289 are cloned in E. coli strain XL-1 Blue according to standard procedures (Sambrook, Fritsch & Maniatis, Molecular Cloning, A Laboratory Manual, 3rd edition, CSHL Press, 2001; Qiagen manual "The QIAexpressionist™", 5$^{th}$ edition, June 2003). Transformed colonies are used to inoculate dYT medium (per 1 H$_2$O 16 g Bacto Trypton, 10 g Bacto Yeast Extract, 5 g NaCl; 25 µM Ampicillin) and overnight cultures are grown in microwell plates (Falcon No. 353227) at 37° C. under continuous shaking (shaker incubator, 150 rounds per minute). 100 µl of an overnight culture is mixed with 100 µl fresh medium and incubated for 1 h. IPTG is added to result in a final concentration of 500 µM and the cultures are incubated for another 4 h. Subsequently, the bacteria are lyzed by mixing the culture with 10% B-PER® solution (e.g. B-PER Protein Extraction Reagents, Pierce) and incubating the mixture at 60° C. for 20 min. The microwell plates are centrifuged at 3,300 rounds per minute (rpm) to clear the lysates. Of each lysate a first 40 µl aliquot is pipetted into an Eppendorf PCR plate (96 cavities with 0.2 ml volume each). The plate is incubated for 35 min at 97° C. in an Eppendorf "Mastercycler gradient" thermocycler. Of each lysate a second 40 µl aliquot is kept at room temperature as a positive control.

Subsequently, 30-40 µl of each lysate (heated lysates as well as controls) are transferred to another microwell plate (Costar No. 3903, 96 cavities) and mixed with a PCR master mix to yield a final volume of 100 µl. The PCR master mix contains 10 µl 10× Taq buffer, dATP, dCTP and dGTP at 0.15 mM each, 0.2 mM dNTP additionally containing LightCycler Red 640-N-hydroxysuccinimide ester—labeled dUTP (equimolar), 0.5 mM MgCl$_2$ (in addition to the Mg Cl$_2$ comprised in the 10× Taq buffer), and 50 pM of a fluorescein-labeled template according to SEQ ID NO.:8 (i.e. 0.5 µl of a solution containing 1.6 µg/µl of the template). The microwell plate is incubated at 72° C. for 60 min to allow for template elongation.

Subsequently, plates are cooled at 4° C. for 10 min. FRET (fluorescence resonance energy transfer) is quantitatively measured using a fluorimeter (Tecan). The excitation wavelength is 485 nm. Measurements of light emission are taken at the wavelength of 635 nm. After background signal is subtracted emission values are a function of residual DNA polymerase activity. For each experiment a relative activity value is calculated by dividing the measurement value of the heated sample by the measurement value of the unheated control sample and multiplying the result with 100. Table 1 summarizes the relative activity values determined in four experiments.

TABLE 1

Relative activity of polypeptides with DNA polymerase activity after 35 min at 97° C.

| Experiment # | TaqΔ288 | TaqΔ279 | TaqΔ289 | TaqWT |
|---|---|---|---|---|
| 1 | 67 | 31 | 18 | −3 |
| 2 | 90 | 36 | 32 | −1 |
| 3 | 62 | 46 | 24 | −3 |
| 4 | 78 | 38 | 28 | 1 |

EXAMPLE 3

Expression and Purification of Polypeptides with DNA Polymerase Activity

A total volume of 4 l of dYT medium, split into 800 ml aliquots in 2 l flasks are inoculated with E. coli strain XL-1 Blue transformed with the pQE80L expression vector (Qiagen catalogue no. 32923) in which the reading frame encoding TaqΔ288, TaqΔ279 (Klentaq), the Stoffel fragment (TaqΔ290), and TaqWT has been inserted. Cells are grown in a shaking culture at 37° C. (shaking incubator, 250 rounds per minute). At an optical density of about 0.8 (measured at 600 nm) IPTG (Isopropylthiogalactoside) is added to a final concentration of 500 µM. Cells are further grown until an optical density of between 2 and 3 is reached. The cells are then sedimented by centrifugation and the pellet is resuspended in B50 buffer (25 mM Tris HCl pH 8.5, 0.1 mM EDTA, 5% glycerol, 1 mM DTT (dithiothreitol), 50 mM NaCl) at room temperature.

Purification Protocol 1

The cells are lysed using a French Press twice at 1,000 bar. NaCl is added to 1.5 M to dissolve polymerases from the DNA. Subsequently, the mixture is heated to 75° C. for 15 min on a water bath. Subsequently, the mixture is left in the water bath without further heating for another 15 min. The precipitate is separated from the supernatant by centrifugation. The supernatant is dialyzed against B100 buffer (25 mM Tris HCl pH 8.5, 0.1 mM EDTA, 5% glycerol, 1 mM DTT, 100 mM NaCl). Subsequently, chromatographic steps are performed. The first step uses a heparin sepharose column and elution of the TaqΔ288 polypeptide by means of gradient elution with B100 and B600 (25 mM Tris HCl pH 8.5, 0.1 mM EDTA, 5% glycerol, 1 mM DTT, 600 mM NaCl). Following dialysis of the TaqΔ288-containing fraction against B50 the enzyme is further purified using a Q sepharose column and for elution a gradient with B50 and B250 (25 mM Tris HCl pH 8.5, 0.1 mM EDTA, 5% glycerol, 1 mM DTT, 250 mM NaCl). Finally the fraction with the eluted TaqΔ288 is dialyzed against storage buffer (50% [v/v] glycerol, 100 mM KCl, 20 mM Tris HCl pH 8.5, 0.1 mM EDTA, 1 mM DTT, 0.25% Thesit).

Purification Protocol 2

Purification is facilitated if the His-tag is used during purification. 5 g sedimented cells are resuspended in 25 ml lysis buffer (50 mM NaH$_2$PO$_4$, 300 mM NaCl, 10 mM imidazole, 0.1 mM PMSF (phenylmethylsulfonyl fluoride), 1 mM DTT, pH 8.0) and lysed using ultrasound. DNase I (Roche Diagnostics GmbH, Mannheim) is added to a final concentration of 20 mg/ml and MgCl₂ to a final concentration of 4 mM. The mixture is incubated at 25° C. for 30 min. Following heat incubation for 30 min at 72° C. the precipitate is sedimented by centrifugation (22,000×g). The cleared supernatant is loaded onto a 10 ml Ni-NTA superflow column (Qiagen). The column is washed with two volumes of buffer A (50 mM NaH₂PO₄, 300 mM NaCl, 10 mM imidazole, pH 8.0). The column is eluted with a volume of 100 ml of a linear gradient, starting with buffer A and ending with buffer B (50 mM NaH₂PO₄, 300 mM NaCl, 250 mM imidazole, pH 8.0). The His-tagged TaqΔ288 polypeptide is further purified by anion exchange chromatography with Q sepharose. Finally, the fraction containing the purified His-tagged TaqΔ288 polypeptide is dialyzed against storage buffer.

In order to remove the His tag, the Ni-NTA purified His-tagged TaqΔ288 polypeptide is dialyzed against Xa reaction buffer (20 mM Tris HCl pH 6.5, 50 mM NaCl, 1 mM CaCl₂). Factor Xa protease (1 U per mg TaqΔ288 polypeptide) is added together with ¹/₁₀ of the total reaction volume of 10× concentrated reaction buffer. The mixture is incubated for 3 to 6 days at 4° C. Subsequently, the pH is raised to 8.0 by adding 1 M Tris HCl pH 8.5 (about ¹/₁₀₀ volume). Further, equilibrated Ni-NTA superflow material is added and the mixture is incubated for 30 min at room temperature under continuous agitation (rotation). The supernatant is separated from the Ni-NTA superflow material with uncleaved His-tagged TaqΔ288 polypeptide and heat-inactivated at 72° C. at 30 min. The following steps are anion exchange chromatography with Q sepharose, followed by dialysis against storage buffer.

EXAMPLE 4

Activity of TaqΔ288

DNA polymerase activity is determined using standard procedures by first hybridizing an M13 primer to M13 mp9ss DNA at 65° C. and then incorporate radioactively labeled α³²dCTP. Incorporation is measured by liquid scintillation counting. The activity is compared to a master lot of TaqWT preparation which serves as a reference. Table 2

TABLE 2

| Specific activities of polypeptides with DNA polymerase activity | |
|---|---|
| TaqWT | ~100 kU/mg |
| TaqΔ288 | ~77 kU/mg |
| TaqΔ279 | ~370 kU/mg |
| TaqΔ290 | ~111 kU/mg |

Regarding the presence or absence of the His tag in the TaqΔ288 polypeptide no differences regarding DNA polymerase activity have been detected.

EXAMPLE 5

Molecular Characterization of TaqΔ288

TaqΔ288 polypeptide without His-tag has been prepared. N-terminal sequencing has revealed the amino acid sequence ESPKALEEAPWPPPE (SEQ ID NO: 10). The molecular weight of the TaqΔ288 polypeptide has been determined as being 62.5 kDa by means of MALDI TOF (matrix-assisted laser desorption/ionization-time of flight) mass spectrometry.

EXAMPLE 6

Citraconylation of TaqΔ288

3 mg of purified His-tagged TaqΔ288 polypeptide in 3 ml reaction buffer (50 mM HEPES, 300 mM KCl, 1 mM EDTA, pH8.5) are reacted with 2 μl of citraconic acid anhydride for 1 h at room temperature. The mixture is subsequently dialyzed against storage buffer (63% [w/v] glycerol, 100 mM KCl, 20 mM Tris HCl pH 8.5, 0.1 mM EDTA, 0.5% Tween 20, 1 mM DTT).

What is claimed is:

1. An isolated polypeptide having DNA polymerase activity and consisting of the amino acid sequence of SEQ ID NO: 2.

2. An isolated polypeptide having DNA polymerase activity and consisting of the amino acid sequence of SEQ ID NO: 4.

3. A fusion polypeptide having the amino acid sequence of SEQ ID NO: 5.

4. The polypeptide of claim 1 covalently coupled to a compound selected from the group consisting of citraconic anhydride, cis-aconitic anhydride, 2,3-dimethylmaleic anhydride, exo-cis-3,6-endoxo-delta 4-tetrahydrophthalic anhydride, and 3,4,5,6-tetrahydrophthalic anhydride.

* * * * *